(12) United States Patent
Murphy et al.

(10) Patent No.: US 9,092,850 B2
(45) Date of Patent: Jul. 28, 2015

(54) IDENTIFYING LOCATION BIOMARKERS

(75) Inventors: Robert F. Murphy, Wexford, PA (US); Arvind Rao, Houston, TX (US); Estelle Glory-Afshar, Atlanta, GA (US); Justin Y. Newberg, Houston, TX (US); Santosh Bhavani, Houston, TX (US); Aparna Kumar, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 159 days.

(21) Appl. No.: 13/980,512

(22) PCT Filed: Jan. 20, 2012

(86) PCT No.: PCT/US2012/022070
§ 371 (c)(1),
(2), (4) Date: Nov. 4, 2013

(87) PCT Pub. No.: WO2012/100190
PCT Pub. Date: Jul. 26, 2012

(65) Prior Publication Data
US 2014/0050385 A1    Feb. 20, 2014

Related U.S. Application Data

(60) Provisional application No. 61/461,694, filed on Jan. 21, 2011.

(51) Int. Cl.
*G06K 9/00* (2006.01)
*G06T 7/00* (2006.01)
*G06F 19/18* (2011.01)
*G01N 33/574* (2006.01)
*G06F 19/24* (2011.01)

(52) U.S. Cl.
CPC ........ *G06T 7/0012* (2013.01); *G01N 33/57484* (2013.01); *G06F 19/18* (2013.01); *G06F 19/24* (2013.01)

(58) Field of Classification Search
None
See application file for complete search history.

(56) References Cited

U.S. PATENT DOCUMENTS

2001/0049114 A1 * 12/2001 Bacus ........................ 435/7.21
2002/0177149 A1 * 11/2002 Rimm et al. ..................... 435/6
2008/0026415 A1 *  1/2008 Rimm et al. .................... 435/15
2008/0032321 A1 *  2/2008 Ginty et al. .................... 435/15
2010/0160177 A1 *  6/2010 Merbl et al. ..................... 506/9

OTHER PUBLICATIONS

Kai et al, "image content-based retrieval and automated interpretation of Fluorescence microscope images via the protein subcellular location image database", IEEE 2001.*

(Continued)

*Primary Examiner* — Amara Abdi
(74) *Attorney, Agent, or Firm* — Fish & Richardson P.C.

(57) ABSTRACT

A method performed by one or more processing devices includes retrieving data for a protein in a tissue type in a first state and for the protein in the tissue type in a second state; determining, based on the retrieved data, first features of the protein in the tissue type in the first state; determining, based on the retrieved, second features of the protein in the tissue type in the second state; and identifying, based on the first features and the second features, that a location of the protein in the tissue type in the first state differs from a location of the protein in the tissue type in the second state.

31 Claims, 14 Drawing Sheets phospho- β-catenin

(56) References Cited

OTHER PUBLICATIONS

Kai Huang et al., "Image Content-Based Retrieval and Automated Interpretation of Fluorescence Microsope Images via the Protein Subcellular Location Image Database," 2002 IEEE International Symposium, pp. 325-328.

International Preliminary Report on Patentability for corresponding Application No. PCT/US2012/022070, dtd. Aug. 1, 2013, pp. 1-6.

* cited by examiner

| Location Biomarker | Gene Name | Exemplary Accession Number |
|---|---|---|
| ABCA10 | ATP-binding cassette, sub-family A (ABC1), member 10 | NM_080282 |
| ABCB4 | ATP-binding cassette, sub-family B (MDR/TAP), member 4 | NM_000443 |
| ABHD15 | abhydrolase domain containing 15 | NM_198147 |
| ACACA | acetyl-CoA carboxylase alpha | NM_198834 |
| ACIN1 | apoptotic chromatin condensation inducer 1 | NM_001164814 |
| ACVR1C | activin A receptor, type IC | NM_001111031 |
| AFP | alpha-fetoprotein | NM_001134 |
| ARID1B | AT rich interactive domain 1B (SWI1-like) | NM_017519 |
| ARSA | arylsulfatase A | NM_000487 |
| ARSD | arylsulfatase D | NM_001669 |
| AS3MT | arsenic (+3 oxidation state) methyltransferase | NM_020682 |
| ATG4C | ATG4 autophagy related 4 homolog C | NM_032852 |
| BARHL1 | BarH-like homeobox 1 | NM_020064 |
| BCL6 | B-cell CLL/lymphoma 6 | NM_001130845 |
| BRD8 | bromodomain containing 8 | NM_006696 |
| BRDT | bromodomain, testis-specific | NM_001242805 |
| BRI3BP | BRI3 binding protein | NM_080626 |
| C11orf30 | chromosome 11 open reading frame 30 | NM_020193 |
| C14ORF118 | chromosome 14 open reading frame 118 | NM_017926 |
| C7ORF68 | chromosome 7 open reading frame 68 | NM_001098786 |
| CAD | carbamoyl-phosphate synthetase 2, aspartate transcarbamylase, and dihydroorotase | NM_004341 |
| CAMP | cathelicidin antimicrobial peptide | NM_004345 |
| CCDC51 | coiled-coil domain containing 51 | NM_024661 |
| CCNT1 | cyclin T1 | NM_001240 |
| CCT2 | chaperonin containing TCP1, subunit 2 (beta) | NM_006431 |
| CD151 | CD151 molecule (Raph blood group) | NM_004357 |
| CDKN2A | cyclin-dependent kinase inhibitor 2A (melanoma, p16, inhibits CDK4) | NM_058195 |
| CEBPB | CCAAT/enhancer binding protein (C/EBP), beta | NM_005194 |
| CPB2 | carboxypeptidase B2 (plasma) | NM_001872 |
| CTAGE1 | cutaneous T-cell lymphoma-associated antigen 1 | NM_172241 |
| CTNNBL1 | catenin, beta like 1 | NM_030877 |
| CTSB | cathepsin B | NM_001908 |
| CTSL2 | cathepsin L2 | NM_001333 |
| CTSS | cathepsin S | NM_004079 |
| DDRGK1 | DDRGK domain containing 1 | NM_023935 |
| DRG1 | developmentally regulated GTP binding protein 1 | NM_004147 |
| DVL1 | dishevelled, dsh homolog 1 | NM_004421 |
| DVL2 | dishevelled, dsh homolog 2 | NM_004422 |
| E2F1 | E2F transcription factor 1 | NM_005225 |
| EEF2 | eukaryotic translation elongation factor 2 | NM_001961 |
| ELF2 | E74-like factor 2 (ets domain transcription factor) | NM_201999 |
| ETV3 | ets variant 3 | NM_001145312 |

FIGURE 11

| FBXO18 | F-box protein, helicase, 18 | NM_032807 |
|---|---|---|
| FOXA3 | forkhead box A3 | NM_004497 |
| FUS | fused in sarcoma | NM_004960 |
| GABPB1 | GA binding protein transcription factor, beta subunit 1 | NM_005254 |
| GLA | galactosidase, alpha | NM_000169 |
| GRK6 | G protein-coupled receptor kinase 6 | NM_002082 |
| GSTZ1 | glutathione transferase zeta 1 | NM_145870 |
| GTF2E1 | general transcription factor IIE, polypeptide 1, alpha 56kDa | NM_005513 |
| GTF2H1 | general transcription factor IIH, polypeptide 1, 62kDa | NM_001142307 |
| GUCY1A2 | guanylate cyclase 1, soluble, alpha 2 | NM_000855 |
| HMG20A | high mobility group 20A | NM_018200 |
| HNF4A | hepatocyte nuclear factor 4, alpha | NM_000457 |
| HNRNPH2 | heterogeneous nuclear ribonucleoprotein H2 (H') | NM_019597 |
| HOXA1 | homeobox A1 | NM_005522 |
| IL18 | interleukin 18 (interferon-gamma-inducing factor) | NM_001562 |
| JMJD6 | jumonji domain containing 6 | NM_001081461 |
| KCNF1 | potassium voltage-gated channel, subfamily F, member 1 | NM_002236 |
| KDM3B | lysine (K)-specific demethylase 3B | NM_016604 |
| LRFN5 | leucine rich repeat and fibronectin type III domain containing 5 | NM_152447 |
| LRIG3 | leucine-rich repeats and immunoglobulin-like domains 3 | NM_001136051 |
| LXN | latexin | NM_020169 |
| MAP1B | microtubule-associated protein 1B | NM_005909 |
| MBNL1 | muscleblind-like | NM_021038 |
| MCM3 | minichromosome maintenance complex component 3 | NM_002388 |
| MCM6 | minichromosome maintenance complex component 6 | NM_005915 |
| MCM7 | minichromosome maintenance complex component 7 | NM_005916 |
| MDC1 | mediator of DNA-damage checkpoint 1 | NM_014641 |
| MECP2 | methyl CpG binding protein 2 (Rett syndrome) | NM_001110792 |
| MEF2D | myocyte enhancer factor 2D | NM_005920 |
| MNAT1 | menage a trois homolog 1, cyclin H assembly factor (Xenopus laevis) | NM_001177963 |
| MPPE1 | metallophosphoesterase 1 | NM_023075 |
| MSTN | myostatin | NM_005259 |
| MYST4 (KAT6B) | K(lysine) acetyltransferase 6B (previously named MYST histone acetyltransferase (monocytic leukemia) 4 )) | NM_012330 |
| NAB2 | NGFI-A binding protein 2 (EGR1 binding protein 2) | NM_005967 |
| NCOA6 | nuclear receptor coactivator 6 | NM_014071 |
| NDRG2 | NDRG family member 2 | NM_201535 |
| NEK11 | NIMA (never in mitosis gene a)- related kinase 11 | NM_024800 |
| NFIA | nuclear factor I/A | NM_001134673 |
| NLRP3 | NLR family, pyrin domain containing 3 | NM_004895 |
| ODR4 | chromosome 1 open reading frame 27 | NM_017847 |
| ORC4L | origin recognition complex, subunit 4 | NM_001190879 |
| PABPC5 | poly(A) binding protein, cytoplasmic 5 | NM_080832 |

FIGURE 11 CONTINUED

| | | |
|---|---|---|
| PBX1 | pre-B-cell leukemia homeobox 1 | NM_002585 |
| PBX3 | pre-B-cell leukemia homeobox 3 | NM_006195 |
| PHYH | phytanoyl-CoA 2-hydroxylase | NM_006214 |
| PIF1 | PIF1 5'-to-3' DNA helicase homolog | NM_025049 |
| PLBD2 | phospholipase B domain containing 2 | NM_173542 |
| POLA1 | polymerase (DNA directed), alpha 1, catalytic subunit | NM_016937 |
| PRKDC | protein kinase, DNA-activated, catalytic polypeptide | NM_006904 |
| PRPF39 | PRP39 pre-mRNA processing factor 39 homolog | NM_017922 |
| PSAP | prosaposin | NM_001042465 |
| PTPRB | protein tyrosine phosphatase, receptor type, B | NM_001109754 |
| RAG1AP1 (SLC50A1) | solute carrier family 50 (sugar transporter), member 1 (previously named recombination activating gene 1 activating protein 1) | NM_018845 |
| RBM5 | RNA binding motif protein 5 | NM_005778 |
| REL | v-rel reticuloendotheliosis viral oncogene homolog | NM_002908 |
| RFC4 | replication factor C (activator 1) 4, 37kDa | NM_002916 |
| RNFT1 | ring finger protein, transmembrane 1 | NM_016125 |
| RPS12 | ribosomal protein S12 | NM_001016 |
| RUNX1 | runt-related transcription factor 1 | NM_001754 |
| RXRA | retinoid X receptor, alpha | NM_002957 |
| RXRB | retinoid X receptor, beta | NM_021976 |
| S100A1 | S100 calcium binding protein A1 | NM_006271 |
| SDCCAG1 (NEMF) | nuclear export mediator factor (previously named serologically defined colon cancer antigen 1) | NM_004713 |
| SDF4 | stromal cell derived factor 4 | NM_016547 |
| SELP | selectin P (granule membrane protein 140kDa, antigen CD62) | NM_003005 |
| SERPINF1 | serpin peptidase inhibitor, clade F (alpha-2 antiplasmin, pigment epithelium derived factor), member 1 | NM_002615 |
| SIL1 | SIL1 homolog, endoplasmic reticulum chaperone | NM_001037633 |
| SMARCB1 | SWI/SNF related, matrix associated, actin dependent regulator of chromatin, subfamily b, member 1 | NM_003073 |
| SMARCC2 | SWI/SNF related, matrix associated, actin dependent regulator of chromatin, subfamily c, member 2 | NM_003075 |
| SNAI1 | snail homolog 1 | NM_005985 |
| SSB | Sjogren syndrome antigen B (autoantigen La) | NM_003142 |
| STAG2 | stromal antigen 2 | NM_001042749 |
| STX17 | syntaxin 17 | NM_017919 |
| STXBP4 | syntaxin binding protein 4 | NM_178509 |
| TARDBP | TAR DNA binding protein | NM_007375 |
| TBX2 | T-box 2 | NM_005994 |
| THRAP3 | thyroid hormone receptor associated protein 3 | NM_005119 |
| TLR9 | toll-like receptor 9 | NM_017442 |
| TMEM132C | transmembrane protein 132C | NM_001136103 |
| TMEM180 | transmembrane protein 180 | NM_024789 |
| TMEM51 | transmembrane protein 51 | NM_001136216 |
| TUBA1 | tubulin, alpha 4a | NM_006000 |
| TUBB3 | tubulin, beta 3 | NM_006086 |

FIGURE 11 CONTINUED

| | | |
|---|---|---|
| TUBB4 | tubulin, beta 4 | NM_006087 |
| TUBG1 | tubulin, gamma 1 | NM_001070 |
| TXN2 | thioredoxin 2 | NM_012473 |
| UGCGL1 | UDP-glucose glycoprotein glucosyltransferase 1 | NM_020120 |
| USP2 | ubiquitin specific peptidase 2 | NM_004205 |
| WDR13 | WD repeat domain 13 | NM_017883 |
| WEE1 | WEE1 homolog | NM_003390 |
| YY1 | YY1 transcription factor | NM_003403 |
| ZBTB16 | zinc finger and BTB domain containing 16 | NM_006006 |
| ZMYM3 | zinc finger, MYM-type 3 | NM_201599 |
| ZNF177 | zinc finger protein 177 | NM_001172651 |
| ZNF200 | zinc finger protein 200 | NM_003454 |
| ZNF275 | zinc finger protein 275 | NM_001080485 |
| ZNF350 | zinc finger protein 350 | NM_021632 |
| ZNF419 | zinc finger protein 419 | NM_001098491 |
| ZNF544 | zinc finger protein 544 | NM_014480 |
| ZNF773 | zinc finger protein 773 | NM_198542 |
| ZSCAN22 | zinc finger and SCAN domain containing 22 | NM_181846 |

FIGURE 11 CONTINUED

IDENTIFYING LOCATION BIOMARKERS

CLAIM OF PRIORITY

This application claims priority under 35 U.S.C. §119(e) to provisional U.S. Patent Application 61/461,694, filed on Jan. 21, 2011, the entire contents of which are hereby incorporated by reference.

GOVERNMENT RIGHTS

This techniques disclosed herein were made with government support under the National Institutes of Health Grant Number U54 RR022241 and National Science Foundation Grant Number EF-0331657. The government has certain rights in the techniques disclosed herein.

BACKGROUND

In an example, a biomarker includes a specific physical trait used to measure effects of or progress of a disease. For example, concentration of a protein in blood may be a biomarker, when the concentration exceeds a threshold level. In this example, the concentration of the protein reflects the severity or the presence of a disease, including, e.g., cancer.

In another example, biomarkers include substances used as indicators of a biological state. In this example, biomarkers can be used to identify healthy or non-healthy cells/tissues, including, e.g., cancerous cells.

SUMMARY

In one aspect of the present disclosure, a method performed by one or more processing devices includes retrieving data for a protein in a tissue type in a first state and for the protein in the tissue type in a second state; determining, based on the retrieved data, first features of the protein in the tissue type in the first state; determining, based on the retrieved, second features of the protein in the tissue type in the second state; and identifying, based on the first features and the second features, that a location of the protein in the tissue type in the first state differs from a location of the protein in the tissue type in the second state.

Implementations of the disclosure can include one or more of the following features. In some implementations, the tissue type in the first state comprises a type of tissue with cancerous cells, and wherein the tissue type in the second state comprises the type of tissue without a measurable amount of cancerous cells. In other implementations, retrieving the data comprises: retrieving, from a data repository, a first image of the protein in the tissue type in the first state and a second image of the protein in the tissue type in the second state.

In still other implementations, processing the data comprises one or more of: performing spectral unmixing on the first and second images; and applying a thresholding technique to the first and second images. In some implementations, the protein identified as having the location in the tissue type in the first state that differs from the location of the protein in the tissue type in the second state comprises a location biomarker.

In other implementations, retrieving the data comprises retrieving a first set of images and a second set of images, wherein the first features are associated with the first set of images, wherein the second features are associated with the second set of images, and wherein identifying comprises: performing nonparametric hypothesis testing on the first set and on the second set; determining a difference between the first set and the second set; and determining, based on the difference, that the protein comprises a location biomarker.

In still other implementations, retrieving the data comprises retrieving a first set of images of the protein and a second set of images of the protein, wherein the first features are associated with the first set of images, wherein the second features are associated with the second set of images, and wherein identifying comprises: generating clusters from the first set, the second set and images of other proteins in the tissue type in the first state and the tissue type in the second state; determining that at least a first image from the first set is assigned to a first cluster; determining that at least a second image from the second set is assigned to a second cluster that differs from the first cluster; and determining, based on the second cluster differing from the first cluster, that the protein comprises a location biomarker.

In some implementations, identifying comprises: generating, based on the first features, a first classification indicative of the location of the protein in the tissue type in the first state; generating, based on the second features, a second classification indicative of the location of the protein in the tissue type in the second state; comparing the first classification to the second classification; determining, based on the comparing, that the first classification differs from the second classification; and determining, based on the first classification differing from the second classification, that the protein comprises a location biomarker.

In other implementations, generating the first classification and the second classification are based on a classifier, and the method further comprises: training the classifier by performing operations comprising: generating a training set of data from images of healthy tissue retrieved from a data repository, wherein the training set comprises data indicative of locations of proteins in the noncancerous tissue; applying a learning algorithm to the training set; and evaluating results of application of the learning algorithm to the training set.

In some implementations, one or more of the first classification and the second classification comprises a classification to a subcellular location, wherein the subcellular location comprises one of a cytoplasm subcellular location, an endoplasmic reticulum (ER) subcellular location, a golgi subcellular location, an intermediate filament subcellular location, a lysosome subcellular location, a membrane subcellular location, a microtubules subcellular location, a mitochondria subcellular location, a nuclear subcellular location, a peroxisome subcellular location, and a secreted subcellular location.

In still other implementations, the tissue type comprises one of: salivary gland tissue; thyroid gland tissue; parathyroid gland tissue; breast tissue; liver tissue; gall bladder tissue; pancreas tissue; adrenal gland tissue; kidney tissue; urinary tract tissue; ovary tissue; fallopian tube tissue; endometrium tissue; placenta tissue; uterine tissue; vaginal tissue; vulva tissue; lateral ventricle wall tissue; cerebral cortex tissue; hippocampus tissue; cerebellum tissue; skin tissue; bone marrow tissue; skeletal muscle tissue; smooth muscle tissue; lymph node tissue; oral mucosa tissue; tonsil tissue; esophagus tissue; bronchus tissue; lung tissue; heart muscle tissue; spleen tissue; stomach tissue; duodenum tissue; small intestine tissue; appendix tissue; colon tissue; rectum tissue; seminal vesicle tissue; prostate tissue; testis tissue; and epidydimis tissue.

In some implementations, the tissue type in the first state comprises a type of tissue with cancer, wherein the cancer comprises one or more of prostate cancer, lung cancer, colon cancer, rectum cancer, urinary bladder cancer, melanoma, non-Hodgkin lymphoma, kidney cancer, renal pelvis cancer, oral cavity cancer, pharynx cancer, leukemia, pancreas cancer, uterine cancer, thyroid cancer, and ovarian cancer.

In yet other implementations, determining the first protein pattern and the second protein pattern comprises: determining, based on processing the data, a first protein pattern for the protein in the tissue type in the first state and a second protein pattern for the protein in the tissue type in the second state. In some implementations, the protein comprises a location biomarker, and the method further comprises: grouping together location biomarkers that are located in a same location of the tissue type of the first state and that are located in a same location of the tissue type of the second state.

In some implementations one or more of the first features and the second features comprise one or more of (i) multi-resolution texture features, (ii) nuclear overlap features, (iii) spacial proximity features, (iv) spatial co-occurrence (Haralick) features, (v) spatial statistics, and (vi) wavelet features. In other implementations, the retrieved data comprises one or more images, and the method further comprises: selecting a portion of an image for processing. In still other implementations, the selected portion comprises one or more of: an increased concentration of visual signals relative to a concentration of other visual signals in other portions of the image; and an increased quality of visual signals relative to a quality of other visual signals in other portions of the image.

In still another aspect of the disclosure, one or more machine-readable media are configured to store instructions that are executable by one or more processing devices to perform operations including i retrieving data for a protein in a tissue type in a first state and for the protein in the tissue type in a second state; determining, based on the retrieved data, first features of the protein in the tissue type in the first state; determining, based on the retrieved, second features of the protein in the tissue type in the second state; and identifying, based on the first features and the second features, that a location of the protein in the tissue type in the first state differs from a location of the protein in the tissue type in the second state. Implementations of this aspect of the present disclosure can include one or more of the foregoing features.

In still another aspect of the disclosure, an electronic system includes one or more processing devices; and one or more machine-readable media configured to store instructions that are executable by the one or more processing devices to perform operations including: retrieving data for a protein in a tissue type in a first state and for the protein in the tissue type in a second state; determining, based on the retrieved data, first features of the protein in the tissue type in the first state; determining, based on the retrieved, second features of the protein in the tissue type in the second state; and identifying, based on the first features and the second features, that a location of the protein in the tissue type in the first state differs from a location of the protein in the tissue type in the second state. Implementations of this aspect of the present disclosure can include one or more of the foregoing features.

All or part of the foregoing can be implemented as a computer program product including instructions that are stored on one or more non-transitory machine-readable storage media, and that are executable on one or more processing devices. All or part of the foregoing can be implemented as an apparatus, method, or electronic system that can include one or more processing devices and memory to store executable instructions to implement the stated functions.

The details of one or more implementations are set forth in the accompanying drawings and the description below. Other features, objects, and advantages will be apparent from the description and drawings, and from the claims.

BRIEF DESCRIPTION OF DRAWINGS

FIG. 11 lists location biomarkers along with gene names and exemplary accession numbers.

Like reference symbols and designations in the various drawings indicate like elements.

DETAILED DESCRIPTION

A system consistent with this disclosure detects location biomarkers in tissue cells. Generally, a location biomarker includes a protein with a location in a tissue type in a first state that differs from a location of the protein in the tissue type in a second state. For example, the tissue type in the first state may include healthy tissue. In this example, the tissue type in the second state may include diseased tissue (e.g., cancerous tissue). As used herein, the terms "cancer" and "cancerous" refer to a physiological condition typically characterized by unregulated cell growth.

The location of the protein may differ in the healthy tissue and in the cancerous tissue, e.g., in normal ovarian tissue the protein is located in the nucleus but is located in the plasma membrane in cancerous ovarian tissue. In this example, the protein is a location biomarker due to the difference in location of the protein in the healthy tissue and in the cancerous tissue.

The system may be configured to detect location biomarkers for various types of tissue, including, e.g., salivary gland tissue; thyroid gland tissue; parathyroid gland tissue; breast tissue; liver tissue; gall bladder tissue; pancreas tissue; adrenal gland tissue; kidney tissue; urinary tract tissue; ovary tissue; fallopian tube tissue; endometrium tissue; placenta tissue; uterine tissue; vaginal tissue; vulva tissue; lateral ventricle wall tissue; cerebral cortex tissue; hippocampus tissue; cerebellum tissue; skin tissue; bone marrow tissue; skeletal muscle tissue; smooth muscle tissue; lymph node tissue; oral mucosa tissue; tonsil tissue; esophagus tissue; bronchus tissue; lung tissue; heart muscle tissue; spleen tissue; stomach tissue; duodenum tissue; small intestine tissue; appendix tissue; colon tissue; rectum tissue; seminal vesicle tissue; prostate tissue; testis tissue; and epididymis tissue.

In this example, types of cancer that may affect at least some of the above-described tissue types include without limitation prostate cancer, lung cancer, colon cancer, rectum cancer, urinary bladder cancer, melanoma, non-Hodgkin lymphoma, kidney cancer, renal pelvis cancer, oral cavity cancer, pharynx cancer, leukemia, pancreas cancer, uterine cancer, thyroid cancer, and ovarian cancer.

Figure 1:
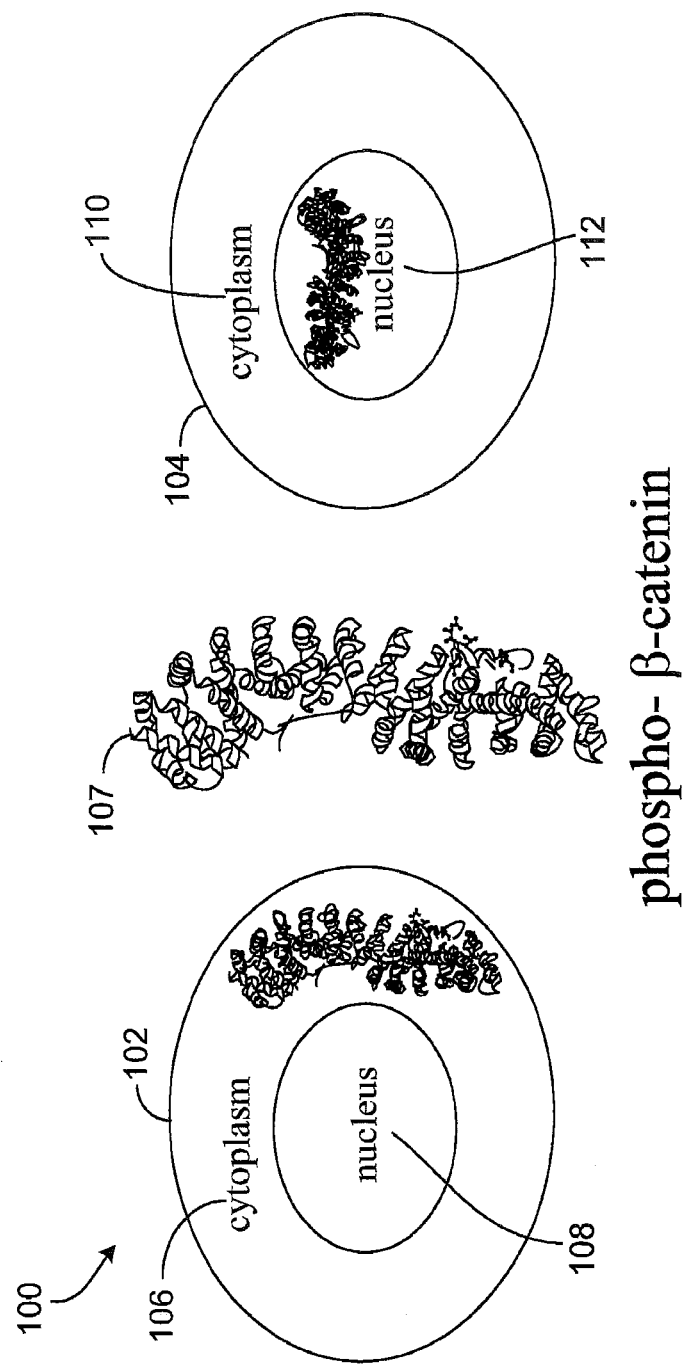
FIG. 1 is a diagram of examples of cells with protein location diversity.

FIG. 1 is a diagram 100 of examples of cells 102, 104 with protein location diversity. Generally, protein location diversity includes a difference in a location of a protein in a tissue type in a first state from a location of the protein in the tissue type in a second state.

Cells 102, 104 both include various proteins, including, e.g., protein 107. Cell 102 includes various locations in which protein 107 may reside, including, e.g., cytoplasm 106 and nucleus 108. Cell 104 also includes various locations in which protein 107 may reside, including, e.g., cytoplasm 110 and nucleus 112.

In the example of FIG. 1, cell 102 includes a cell in healthy tissue (not shown), and cell 104 includes a cell in diseased tissue (not shown). In cell 102, protein 107 is located in cytoplasm 106. In cell 104, protein 107 is located in nucleus 112. In this example, protein 107 is a location biomarker, as the location of protein 107 differs between cell 102 and cell 104.

Figure 2:
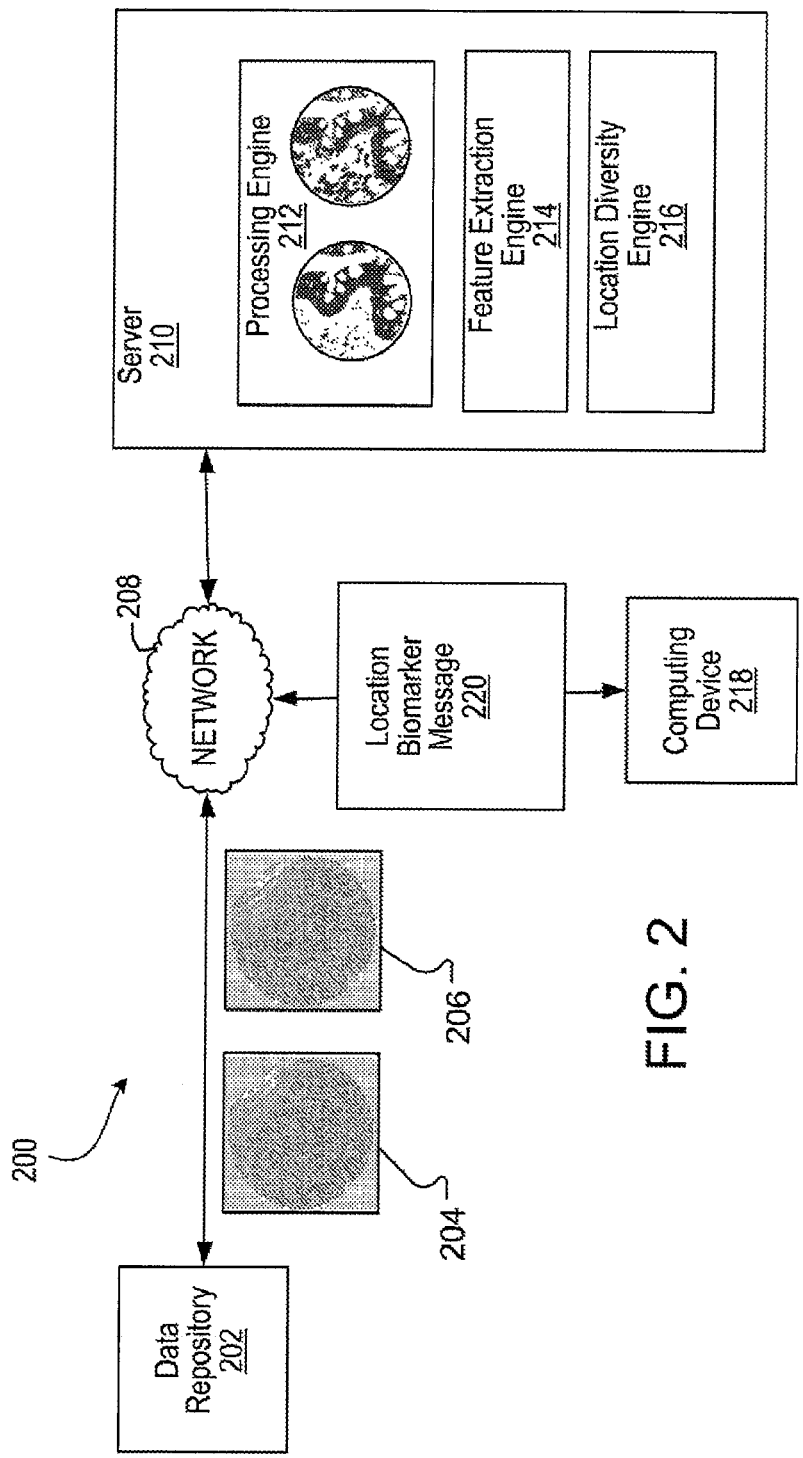
FIG. 2 is a diagram of an example of a network environment for detecting location biomarkers.

FIG. 2 is a diagram of an example of a network environment 200 for detecting location biomarkers. Network environment 200 includes server 210, data repository 202, network 208 and computing device 218.

Computing device 218 and data repository 202 can each communicate with server 210 over network 208. Network environment 200 may include many thousands of data repositories, computing devices and servers, which are not shown.

Server 210 includes various data engines, including, e.g., processing engine 212, feature extraction engine 214, and location diversity engine 216, each of which are described in further detail below. Although each of engines 212, 214, 216 are each shown as a single components in FIG. 2, each of engines 212, 214, 216 can exist in one or more components, which can be distributed and coupled by network 208.

In the example of FIG. 2, data repository 202 is configured to store immunohistochemical images. Generally, an immunohistochemical image includes an image of a tissue that has been stained with antibodies or antisera for identifying patterns of antigen distribution within the tissue.

For example, data repository 202 may include the Human Protein Atlas (HPA). In this example, the HPA includes an online repository of the location patterns of 11,000 proteins in forty-five different tissue types. The HPA includes healthy and cancer images of seven tissues types, including, e.g., pancreas tissue, urinary bladder tissue, kidney tissue, breast tissue, prostate tissue, thyroid tissue, and lung tissue.

For a type of healthy tissue, the HPA includes three images of the healthy tissue stained with monospecific antisera against a specific protein. For cancer tissue, the HPA includes twelve images per protein. An image stored in the HPA may be of a predetermined size, including, e.g., 3000×3000 pixels. Additionally, an image stored in the HPA may be a composite of two stains. A first type of stain (e.g., a purple hematoxylin dye) is used for staining DNA in the tissue. A second type of stain is used for the staining of protein in the tissue. In this example, the second type of stain includes a brown product of diaminobenzidine in the presence of horse-radish peroxidase conjugated to an antibody specific to the protein. Other stains suitable for DNA and protein are well known to those of ordinary skill in the art.

In the example of FIG. 2, data repository 202 includes images 204, 206. Image 204 includes an image of a tissue type in first state, including, e.g., healthy lung tissue. Image 206 includes an image of the tissue type in a second state, including, e.g., cancerous lung tissue. The tissues depicted in images 204, 206 have been stained in various dyes to promote identification of DNA and of various proteins in the tissues.

In an example, server 210 sends a request (not shown) via network 208 to data repository 202 for images 204, 206. In response, data repository 202 sends images 204, 206 to server 210. In this example, the request may be for an image of a tissue type in a first state and another image of the same tissue type in a second, different state.

In response to receipt of images 204, 206, server 210 is configured to perform various operations in detecting whether proteins in the requested tissue types include location biomarkers. To promote detection of location biomarkers, server 210 includes processing engine 212, feature extraction engine 214, and location diversity engine 216. When server 210 detects a location biomarker in a tissue type, server 210 generates location biomarker message 220 to notify a user of computing device 218 of the identified location biomarker. In this example, servers 210 transmits location biomarker message 220 to computing device 218 via network 208.

In an example, processing engine 212 is configured to identify DNA and protein patterns in images 204, 206, as described in further detail below. Feature extraction engine 214 is configured to use the identified DNA and protein patterns in determining features of the tissue types depicted in images 204, 206, as described in further detail below. Location diversity engine 216 is configured to identify, based on the determined features, a diversity (e.g., a difference) in a location of one or of the proteins in the tissue type in the first state depicted in image 204 from a location of the protein in the tissue type in the second state depicted in image 206, as described in further detail below.

Processing engine 212 is configured to identify DNA and protein patterns in images 204, 206, e.g., through application of a thresholding technique and a spectral unmixing technique. Generally, the spectral unmixing technique includes an operation in which a measured spectrum of a mixed pixel is decomposed into (i) a collection of constituent spectra, or endmembers, and (ii) a set of corresponding fractions that indicate a proportion of each endmember present in the pixel. In an example, processing engine 212 performs the spectral unmixing technique by applying a non-negative matrix factorization technique to images 204, 206 to obtain DNA and protein images.

Generally, the thresholding technique includes an operation in which individual pixels in an image are marked as object pixels if values of the pixels are greater than a threshold value and as background pixels if values of the pixels are less than the threshold value. In an example, processing engine 212 may apply the thresholding technique to generate a binary image from a gray scale image.

Figure 3:
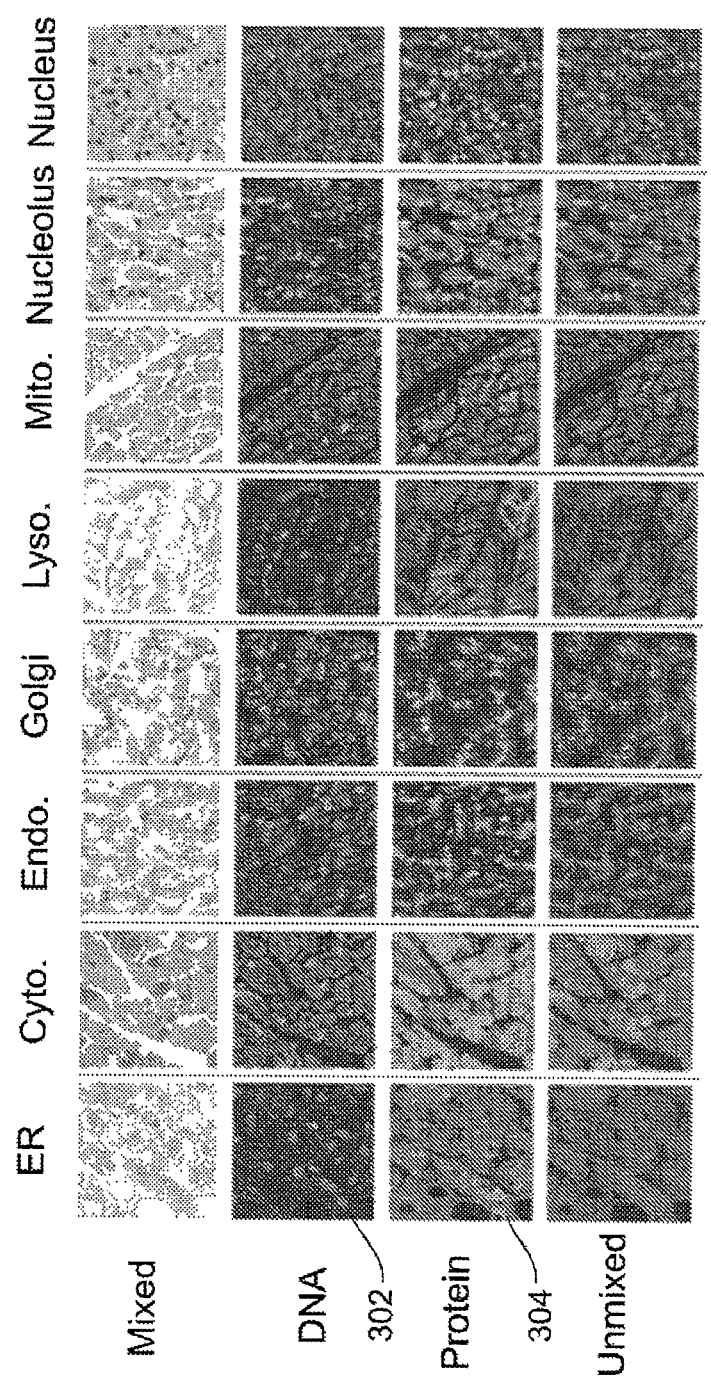
FIG. 3 is a diagram of examples of DNA images and protein images obtained through application of a spectral unmixing technique.

FIG. 3 is an example of DNA images 302 and protein images 304 obtained through application by processing engine 212 of the spectral unmixing technique. In the example of FIG. 3, processing engine 212 generates DNA image 302 and protein image 304 by applying the spectral unmixing technique to image 204. In an example, images 302, 304 include gray scale images of image 204. Processing engine 212 also applies the spectral unmixing technique to image 206, e.g., to generate DNA and protein images (not shown) from image 206.

Figure 4:
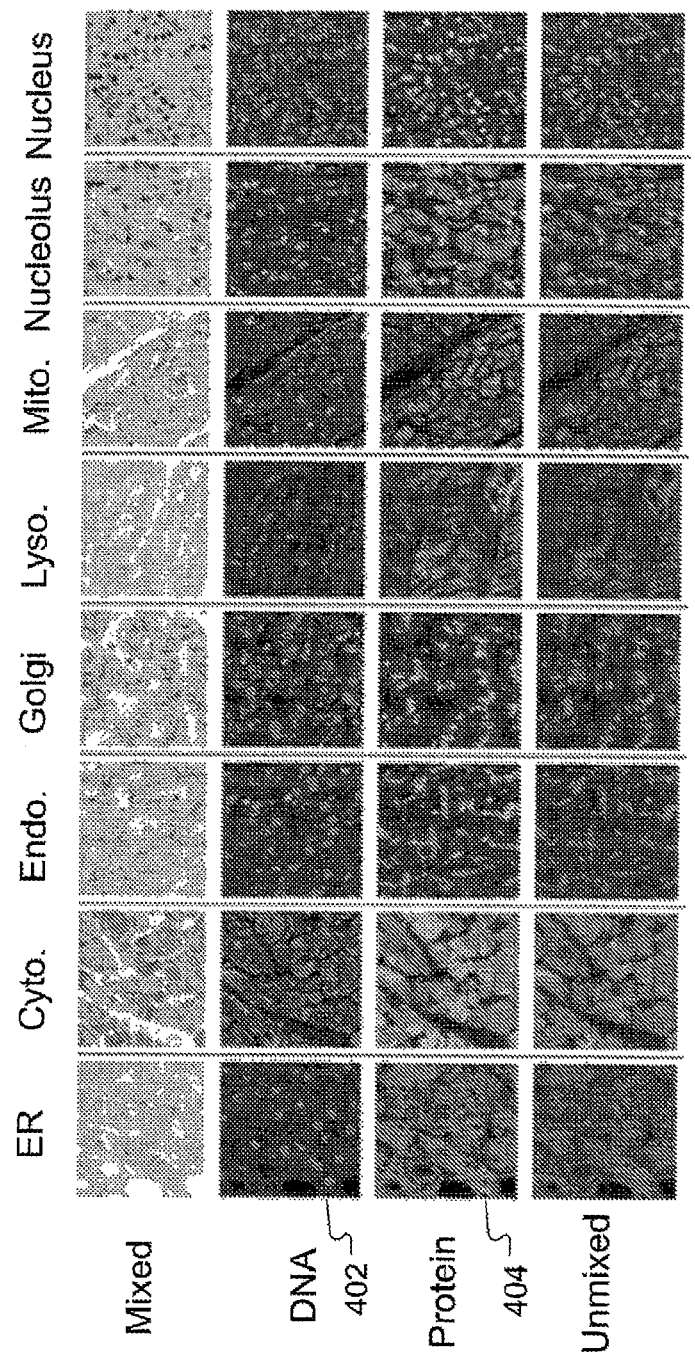
FIG. 4 is a diagram of examples of DNA images and protein images obtained through application of a thresholding technique.

FIG. 4 is an example of DNA image 402 and protein image 404 obtained through application by processing engine 212 of the thresholding technique. In the example of FIG. 4, processing engine 212 converts images 302, 304 to binarized DNA and protein images 402, 404 using the thresholding technique, e.g., the Otsu thresholding technique, as described in "A threshold selection method from gray-level histograms," N. Otsu, IEEE Transactions on System, Man, and Cybernetics 3:6266 (1979). Processing engine 212 also applies the thresholding technique to gray-scale DNA and protein images (not shown) of image 206 to generated binarized DNA and protein images of the tissue depicted in image 206.

Based upon generation of images 402, 404, processing engine 212 identifies DNA and protein patterns in image 204. Using images 402, 404 generated through application of the spectral unmixing technique and the thresholding technique, processing engine 212 determines pixels that are above a threshold used in the thresholding technique. For example, processing engine 212 analyzes image 402 to determine pixels that are above the threshold (e.g., above-threshold pixels). Using the above-threshold pixels in image 402, processing engine 212 identifies a DNA pattern (e.g., $\pi_D$) in the tissue depicted by image 204. Processing engine 212 also analyzes image 404 to determine the above-threshold pixels for the protein in the tissue depicted by image 204. Using the above-threshold pixels in image 404, processing engine 212 identifies a protein pattern (e.g., $\pi_P$) in the tissue depicted by image 204. Processing engine 212 performs similar operations on image 206 to identify the DNA and protein patterns in the tissue depicted in image 206.

Because several proteins may have a partial nuclear localization, $\pi_D \cap \pi_P \neq \emptyset$, in general. Pixels that are common to both the DNA and protein patterns are randomly assigned to one of the patterns, such that a pixel belongs to either the DNA pattern or the protein pattern. Processing engine 212 transmits the DNA and protein patterns to feature extraction engine 214.

Feature Extraction Engine

In an example, feature extraction engine 214 is configured to identify various features of a protein. In this example, the features are indicative of spatial features of the DNA and protein patterns, as well as the relationship between the DNA and protein patterns. In this example, the types of identified features include (i) multiresolution texture features, (ii) nuclear overlap features, (iii) spacial proximity features, (iv) spatial co-occurrence (Haralick) features, (v) spatial statistics, and (vi) wavelet features. In an example, feature extraction engine 214 is configured to determine the above-described features for each image of each protein in data repository 202.

Multiresolution Texture Features

In an example, feature extraction engine 214 is configured to generate multiresolution texture features from gray-scale images, including, e.g., images 302, 304. Generally, multiresolution texture features include texture features calculated after spatially down sampling an image to various extents. In an example, feature extraction engine 214 determines multiresolution texture features by generating a gray-level co-occurrence matrix on the sub bands, for a level of decomposition in one or more of images 302, 304. As described in further detail below, Haralick texture features may be computed using the co-occurrence matrix.

Nuclear Overlap Features

In an example, feature extraction engine 214 is configured to generate nuclear overlap features from binarized images, including, e.g., images 402, 404. Generally, nuclear overlap features include features that capture the relationship between the protein image and the DNA region (e.g., protein staining regions that overlap with the nucleus of the cell). For example, a nuclear overlap feature may include a fraction of an above threshold protein area to an above threshold DNA area, a fraction of the protein fluorescence that co-localizes with DNA, an average distance (in pixels) between above threshold protein pixels, and so forth.

Spacial Proximity Features

Feature extraction engine 214 is configured to determine spacial proximity features, including, e.g., indicators of a spatial association between the DNA and the protein patterns in binarized images (e.g., images 402, 404). Feature extraction engine 214 determines various types of spacial proximity features, including, e.g., metrics indicative of a cost of a spectral cut, commute time distributions, and cluster validity statistics, each of which are described below in further detail.

In computing spacial proximity features, feature extraction engine 214 may implement a clustering algorithm to generate an optimal cluster (e.g., $\pi_1$ and $\pi_2$) of two disjoint sets of data points (e.g., the pixels in images 402, 404). By comparing the optimal cluster $\pi_1, \pi_2$ to pre-specified clusters (e.g., $\pi_D, \pi_P$), feature extraction engine 214 can determine various spatial proximity features.

For example, feature extraction engine 214 may generate cluster validity statistics by comparing the pre-specified clusters ($\pi_D, \pi_P$) to the optimal cluster ($\pi_1, \pi_2$). Feature extraction engine 214 may also generate a metric indicative of a cost of spectral cut, which involves quantifying the inter-cluster association and the cluster associations for pre-specified clusters ($\pi_D, \pi_P$) or optimal clusters ($\pi_1, \pi_2$). Feature extraction engine 214 may also generate commute time metrics, including, e.g., a measure of separateness or spatial heterogeneity of a point pattern in pre-specified clusters ($\pi_D, \pi_P$) in comparison to the spatial heterogeneity of the point pattern in the optimal clusters ($\pi_1, \pi_2$).

Cluster Validity Statistics

In an example, feature extraction engine 214 generates cluster validity statistics using various measures indicative of an agreement between two clusters, including, e.g., Cohen's kappa coefficient, the Rand Index, the Mirken Index, the Huber Index, the Jaccard Index, entropy of the clusters, and so forth.

In an example, Cohen's kappa coefficient is a statistical measure of agreement for categorical items. In this example, Cohen's kappa coefficient of two clusters measures the chance corrected agreement between the two clusters.

To determine Cohen's kappa coefficient, feature extraction engine 214 generates two different two-way clusters designated cluster A and cluster B. In this example, $N_{11}$ represents a number of point pairs in a same cluster under both A and B. $N_{00}$ represents a number of point pairs in different clusters under both A and B. $N_{10}$ represents a number of point pairs in the same cluster under A but not B. $No_{01}$ represents number of point pairs in the same cluster under B but not A, and $N=N_{00}+N_{10}+N_{01}+N_{11}$.

In this example, cluster A corresponds to an original partition of the pixels ($\pi_D, \pi_P$), and cluster B corresponds to the optimal partition ($\pi_1, \pi_2$), obtained from a cluster method. $P_e$ is the probability of expected agreement between the two clusters A and B, given by $$P_e = \frac{(N_{00} + N_{11})}{N}$$

and $P_o$ is the observed probability of cluster agreement, $$P_o = \frac{(N_{00} + N_{01})(N00 + N10)}{N^2} + \frac{(N_{10} + N_{11})(N_{01} + N_{11})}{N^2}.$$

In this example, Cohen's kappa coefficient is given by the following equation:

$$\kappa = \frac{P_o - P_e}{1 - P_e}.$$

Feature extraction engine 214 is also configured to calculate the Rand Index (RI) (and the Adjusted Rand Index), which are another measure for the probability of cluster agreement, given by, $$RI = \frac{(N_{00} + N_{11})}{N(N-1)/2}.$$

Feature extraction engine 214 may also be configured to calculate the Mirkin Index (MI), which quantifies the probability of disagreement, and is related to the Rand Index by, MI=N(N−1)[1−RI]. Feature extraction engine 214 may also be configured to calculate the Huber Index (HI) using the following equation: HI=RI−MI.

Feature extraction engine 214 may also be configured to calculate the Jaccard Index based on the following equation:

$$J_{AB} = \frac{N_{11}}{N_{11} + N_{01} + N_{10}}.$$

Feature extraction engine 214 may also be configured to calculate entropy of the DNA cluster, with mixing distribution given by the following of equation:

$$P_D = \left[ \frac{|\Pi_D \cap \Pi_1|}{|\Pi_D|}, \frac{|\Pi_D \cap \Pi_2|}{|\Pi_D|} \right].$$

In this example, an entropy having a value of zero denotes concordance between the two clusters A and B. In another example, an entropy having a value of $\log_2(2)$ denotes maximal discordance between the original cluster A and the optimal cluster B. Entropy of the protein cluster with mixing distribution is given by the following equation:

$$P_P = \left[ \frac{|\Pi_P \cap \Pi_1|}{|\Pi_P|}, \frac{|\Pi_P \cap \Pi_2|}{|\Pi_P|} \right].$$

Cost of Association and Commute Time Distributions

In an example, feature extraction engine 214 is configured to compute the cost of association of the two clusters $\pi_D$ and $\pi_P$, e.g., using a paradigm of spectral cluster. In this example, the association cost is (inversely proportional to) the commute time along a graph spanning the point set $\pi_D \cup \pi_P$. Commute time distributions are obtained from a k-nearest neighbor graph spanning V=$\pi_D \cup \pi_P$. In this example, the k-nearest neighbor graph is denoted G=(V, E). Feature extraction engine 214 obtains commute times by counting the number of hops along G from a random point in $\pi_D$ to a random point in $\pi_P$ (DNA-protein commute time), or from a random point in $\pi_P$ to a random point in $\pi_P$ (protein-protein commute time), or from a random point in $\pi_D$ to a random point in $\pi_D$ (DNA-DNA commute time). In an example, the commute time depends on the eigenvalues of the Laplacian of the k-nearest neighbor graph.

The commute time CTuv(u, v) between two nodes u and v is given by $$CTuv(u, v) = vol \sum_{j=2}^{n} \left[ \frac{\phi_j(u)}{\lambda_j^2} - \frac{\phi_j(v)}{\lambda_j^2} \right]$$

where $\lambda_j$ and $\theta_j$ are the $j^{th}$ (smallest) eigenvalue and eigenvector of the graph Laplacian L=D−W, and vol is the volume of the graph G, given by vol=$\Sigma_v d_v$, where $d_v$ is the degree of vertex v of the graph. In this example, the commute time $CT_{uv}(u, v)$ is not symmetric, and the symmetrized version is used:

$$CT(u, v) = \frac{(CT_{uv}(u, v) + CT_{uv}(u, v))}{2}$$

for computing these proximity features. In this example, feature extraction engine 214 is configured to generate a commute time distribution FDP (t) from B=1000 randomly drawn sets of point pairs, as shown in the below Table 1.

TABLE 1

Data: point sets $\Pi_D$, $\Pi_P$; k-nearest neighbor graph: G
Result: DNA-protein commute-time distribution: FDP (t)
initialization
for i=1:B (here, B=1000) do
Pick a random point $g_1;_i \in \Pi_D$
Pick a random point $g_2;_i \in \Pi_P$
Compute $CT(g_{1,i}, g_{2,i})$ along the k-nearest neighbor graph G.
end
$F_{DP}$ (t) = P(CT($g_{1,i}, g_2;_i$) ≤ t)

In this example, feature extraction engine 214 is configured to derive the mean commute time, mean-CT ($\pi_D$, $\pi_P$), from the distribution shown in the above Table 1. In one example, if both the random points $g_{1,i}$ and $g_{2,i}$ are picked within the same point set $\pi_D$, then feature extraction engine 214 generates DNA-to-DNA commute time distributions and protein-to-protein commute distributions when $(g_{1,i}, g_{2,i}) \in \pi_P$. These distributions give an indication of the within cluster pattern (DNA/protein) and between-cluster proximities in the images 204, 206. In this example, the DNA and protein patterns are similarly localized, and the mean commute times are relatively small. In another example, mean commute times with increased values indicate a non-overlapping co-localization between DNA and protein patterns of the composite images 204, 206.

Using the paradigm of spectral cluster, feature extraction engine 214 computes the cost of association of the two clusters (point patterns) $\pi_P$ and $\pi_D$ in accordance with the following equation:

$$Nassoc(A, B) = \frac{assoc(\Pi_D, \Pi_D)}{assoc(\Pi_P \cup \Pi_D, \Pi_D)} + \frac{assoc(\Pi_P, \Pi_P)}{assoc(\Pi_P \cup \Pi_D, \Pi_P)}.$$

Feature extraction engine 214 also computes a cost of association-cut in accordance with the following equation: Ncut (A,B)=2−Nassoc (A,B). In this example, assoc($\pi_D$, $\pi_P$) is inversely proportional to the mean commute time of traversing from a random point in point-set $\pi_D$ to a random point in point-set $\pi_P$.

In an example, the techniques described above can be applied to all or part of images 204, 206. For example, a 300 pixel×300 pixel circular subwindow at the center of images 204, 206 may be used in computing the above-described features.

In another example, feature extraction engine 214 is configured select a portion of images 204, 206, e.g., based on various factors. In an example, the selected portion includes an increased concentration of visual signals relative to a concentration of other visual signals in other portions of the image. Generally, visual signals include data indicative of characteristics of a cell, including, e.g., a location of protein, a location of DNA, and so forth. Visual signals may also include data indicative of an amount of dye, e.g., due to the staining of images 204, 206 with dye to stain the protein and the DNA patterns.

In another example, feature extraction engine 214 selects a portion of images 204, 206 with an increased quality of visual signals relative to a quality of other visual signals in other portions of the image.

Spatial Co-occurrence Features

In an example, feature extraction engine 214 is configured to use spatial co-occurrence features in quantifying proximity characteristics of two patterns, including, e.g., $\pi_D$, $\pi_P$. In this example, spatial co-occurrence features include statistical descriptors of the gray-level co-occurrence matrix within an image or across two images (e.g., Haralick features). In determining spatial co-occurrence features, feature extraction engine 214 computes a Euclidean distance transform (EDT) of the two patterns. Feature extraction engine 214 also determines gray-level joint representations in image space (e.g., in images 402, 404) in order to examine the statistical properties of the spatial proximity of the two patterns (DNA and protein). In an example, feature extraction engine 214 is configured to execute the algorithm depicted in the below Table 2 in determining spatial co-occurrence features.

TABLE 2

Figure 5:
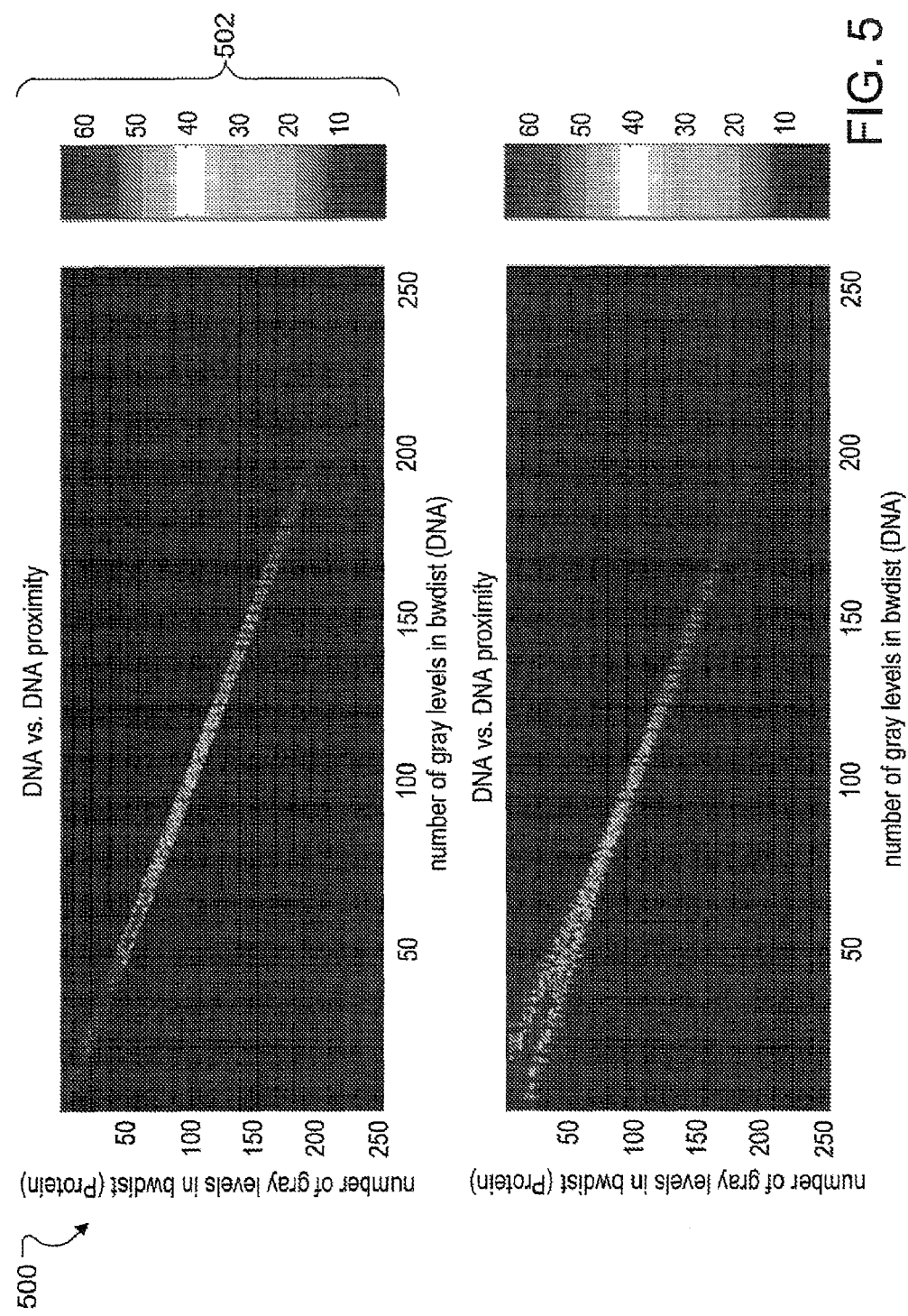
FIGS. 5-6 are diagrams of spatial co-occurrence matrices for patterns of protein localization.
Figure 6:
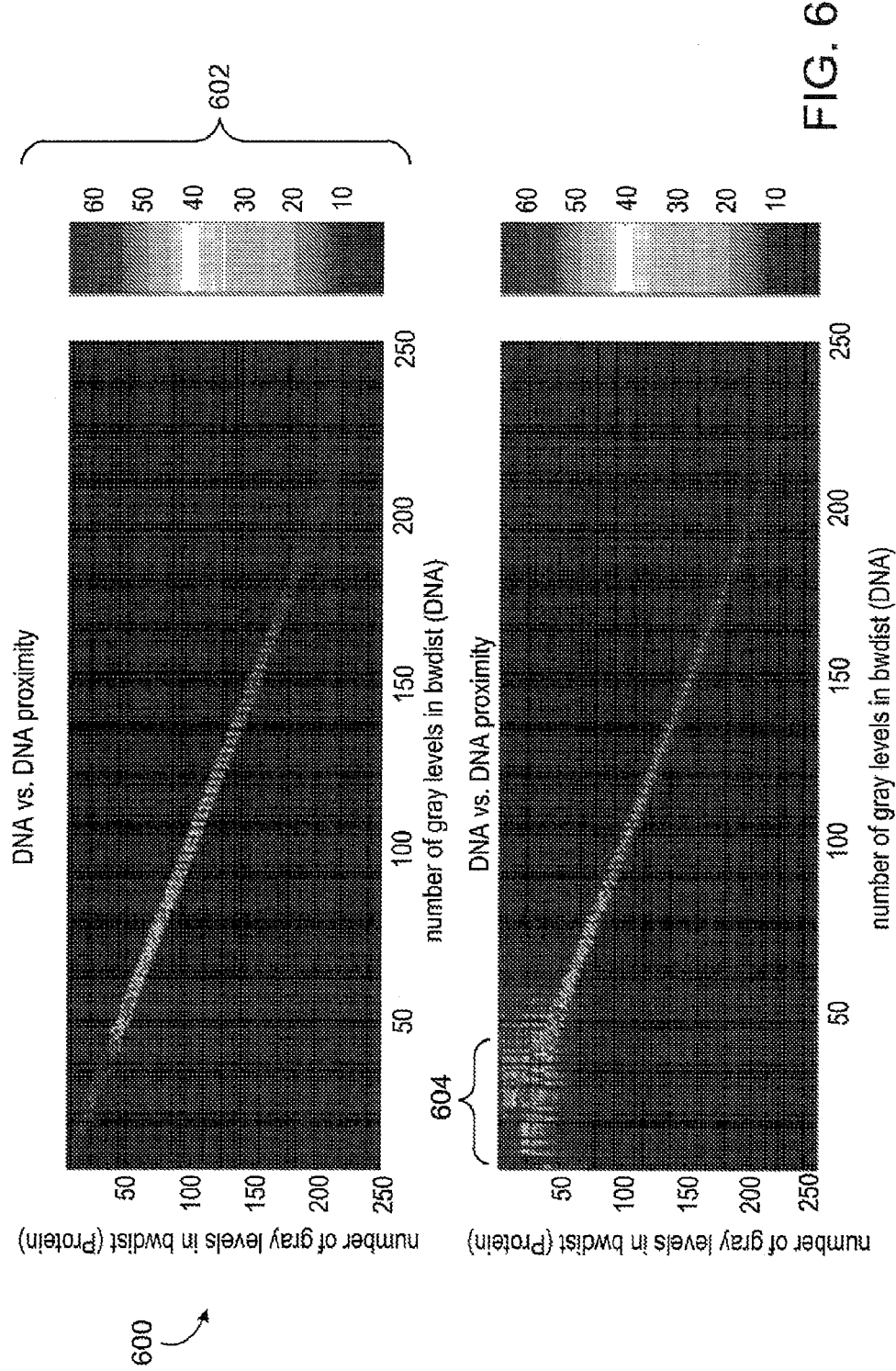

Data: Images: I$_1$ = mat2gray(bwdist($\Pi_D$)), I$_2$ = mat2gray(bwdist($\Pi_P$))
Result: Spatial Co-Occurrence Matrix: CO (I$_1$, I$_2$)
initialization;
[r,c] = size(I$_1$);% same as size (I$_2$)
for i = 1:r do
  for j=1:c do
    v1 = I$_1$ (i,j)
    v2 = I$_2$ (i,j)
    CO(v1, v2) = CO(v1, v2) + 1;
  end
end Using the computations illustrated in the above Table 2, feature extraction engine 214 generates spatial co-occurrence matrices. FIG. 5-6 show diagrams 500, 600, respectively, of the spatial co-occurrence matrices for patterns of protein localization (e.g., nuclear and mitochondrial localization). Portions 502, 602 of diagrams 500, 600 denote the co-occurrence matrix when the corresponding protein has the same location as the DNA pattern, i.e., when $\pi_D=\pi_P$. Portions 504, 604 of diagrams 500, 600 illustrate that the area of top left corner varies correspondingly with the type of location pattern.

Feature extraction engine 214 is configured to analyze the correlation with the use of texture features. In an example, feature extraction engine 214 is configured to derive a gray-level co-occurrence histogram from pattern images for each of four principal directions (e.g., vertical, horizontal and two diagonals). In this example, Haralick features are related to the statistical properties derived from these joint co-occurrence histograms. Haralick features are computed on the four histograms depicted in diagrams 500, 600 and 524 averaged to yield a total of thirteen features for a $\pi_D$-$\pi_P$ pair within an image (e.g., images 204, 206).

Spatial Statistics

In another example, feature extraction engine 214 is configured to determine spatial statistics, including, e.g., a spatial association between the DNA and protein patterns using segregation measures. Generally, a segregation measure describes an association of one species with itself or with other species. In generating segregation measures, feature extraction engine 214 is configured to construct a contingency table of two species, e.g., as illustrated in the below Table 3.

TABLE 3

| | Label of Nearest Neighbor | | |
|---|---|---|---|
| Label of point | D | P | Total |
| D | N$_{DD}$ | N$_{EP}$ | N$_D$ |
| P | N$_{PD}$ | N$_{PP}$ | N$_P$ |
| Total | n$_D$ | n$_P$ | N |

In the above Table 3, the number of cases where a pixel i is a neighbor of a pixel j is denoted by Nij. For a two-species spatial pattern ($\pi_D$, $\pi_P$), the Dixon measure applied to the segregation of $\pi_D$ is in accordance with the following equation:

$$S_D = \log\left\{\frac{[(N_{DD}/(N_D - N_{DP})]}{[(N_D - 1)/(N - N_D)]}\right\},$$

where N$_D$ is the number of points in $\pi_D$, and N$_{DD}$ is the number of co-occurrences of a DNA pixel in the neighborhood of another DNA pixel. N is the total number of (above threshold) pixels. In this example, a value of S$_D$ greater than zero indicates species segregation. A value of S$_D$ equal to one indicates maximal segregation. Values of S$_D$ closer to zero indicate random association between the two species.

In another example, feature extraction engine 214 is configured to generate a pairwise segregation index S$_{DP}$ between $\pi_D$, $\pi_P$ in accordance with the following equation:

$$S_{DP} = \log\left\{\frac{[(N_{DP}/(N_D - N_{DP})]}{[(N_D)/(N - N_P) - 1]}\right\}.$$

In this example, a value of S$_{DP}$ of zero indicates that the co-occurrences of the two species N$_{DP}$ is the same as would be expected under random labeling. A value greater than or less than zero indicates statistical significance of association.

In still another example, feature extraction engine 214 is configured to execute a neighbor-specific test in accordance with the following equation:

$$z_{DP} = \frac{(N_{DP} - EN_{DP})}{\sqrt{Var(N_{DP})}}$$

In this example, $E[N_{DP}]$ is the expected count in the contingency table. Both $S_{DP}$ and $z_{DP}$ are 2×2 matrices, and the feature vector derived from these statistics is the vectorized form of these two matrices. By concatenating these matrix entries, feature extraction engine 214 obtains an 8-dimensional spatial-statistic feature vector for the $\pi_D$-$\pi_P$ species.

Wavelet Features

In another example, feature extraction engine 214 is configured to generate wavelet features. Generally, wavelets are types of functions used to represent signals. Any signal can be approximated using a combination of these functions. In an example, a function called daubechies wavelet is used to represent (or decompose) the image. After expressing the image in terms of these functions, numbers indicative of the energy of the representation are computed. These numbers computed from the representation are referred to as features. Because the function chosen for representation are "wavelets", the features are referred to as wavelet features.

In this example, feature extraction engine 214 applies Euclidean distance transforms (EDT) to the $\pi_D$ and $\pi_P$ patterns, e.g., that are determined from images 402, 404. Using wavelet packet decomposition methods, feature extraction engine 214 computes five-levels of the Daubechies-12 decomposition on the EDT of the DNA and protein images, including, e.g., images 402, 404. Feature extraction engine 214 may also be configured to compute the approximation and detail coefficients from the 2-D wavelet decomposition of images 402, 404. Additionally, feature extraction engine 214 uses the distances between the transform coefficients of images 402, 404 to quantify the similarity in proximity characteristics (along the vertical and horizontal directions) of the DNA and protein patterns.

Location Diversity Engine

After obtaining the features listed above for images 204, 206, location diversity engine 216 is configured to identify location biomarkers, including, e.g., proteins with different locations between healthy tissue and cancer tissue. Location diversity engine 216 implements various techniques in identifying location biomarkers, including, e.g., a nonparametric hypothesis testing technique, a classification technique, and a hierarchical clustering technique, each of which are described in further detail below.

Nonparametric Hypothesis Testing

In an example, location diversity engine 216 is configured to implement a nonparametric hypothesis testing technique, including, e.g., Friedman-Rafsky (FR) and k-nearest neighbor (kNN) techniques. In this example, a FR test is used to determine if the distribution of the image features within the healthy tissue is significantly different from the distribution of image features within the cancer tissue. As previously described, data repository 202 includes multiple images for a protein that is found in a tissue. Since each protein is represented by multiple images, the FR test is used to test a hypothesis that a distribution of image features within the healthy tissue is equal to the distribution of image features within the cancer tissue.

In another example, location diversity engine 216 executes the k-NN nonparametric hypothesis test to identify equality of distributions. Based on the FR test and the k-NN test, location diversity engine 216 generates a "p-value," including, e.g., a probability of obtaining a test statistic at least as extreme as the one that was actually observed. Location diversity engine 216 identifies as location biomarkers the proteins that are significantly different between healthy and cancer tissue, e.g., based on the p-values associated with the proteins.

Classification

In an example, location diversity engine 216 is configured to use a classification technique in determining location biomarkers. Location diversity engine 216 is configured to implement various types of classification techniques, including, e.g., linear classifiers (e.g., a Naive Bayes classifier), quadratic classifiers, k-nearest neighbor classifiers, decision trees (e.g., random forests), neural networks, Bayesian networks, hidden Markov models, learning vector quantization classifiers, and so forth.

In an example, location diversity engine 216 uses the features of a protein to classify the protein as being located in one of a number of pre-defined locations of a cell, including, e.g., subcellular locations. There are various types of subcellular locations, including, e.g., a cytoplasm subcellular location, an endoplasmic reticulum (ER) subcellular location, a golgi subcellular location, an intermediate filament subcellular location, a lysosome subcellular location, a membrane subcellular location, a microtubules subcellular location, a mitochondria subcellular location, a nuclear subcellular location, a peroxisome subcellular location, a secreted subcellular location, and so forth.

Figure 7:
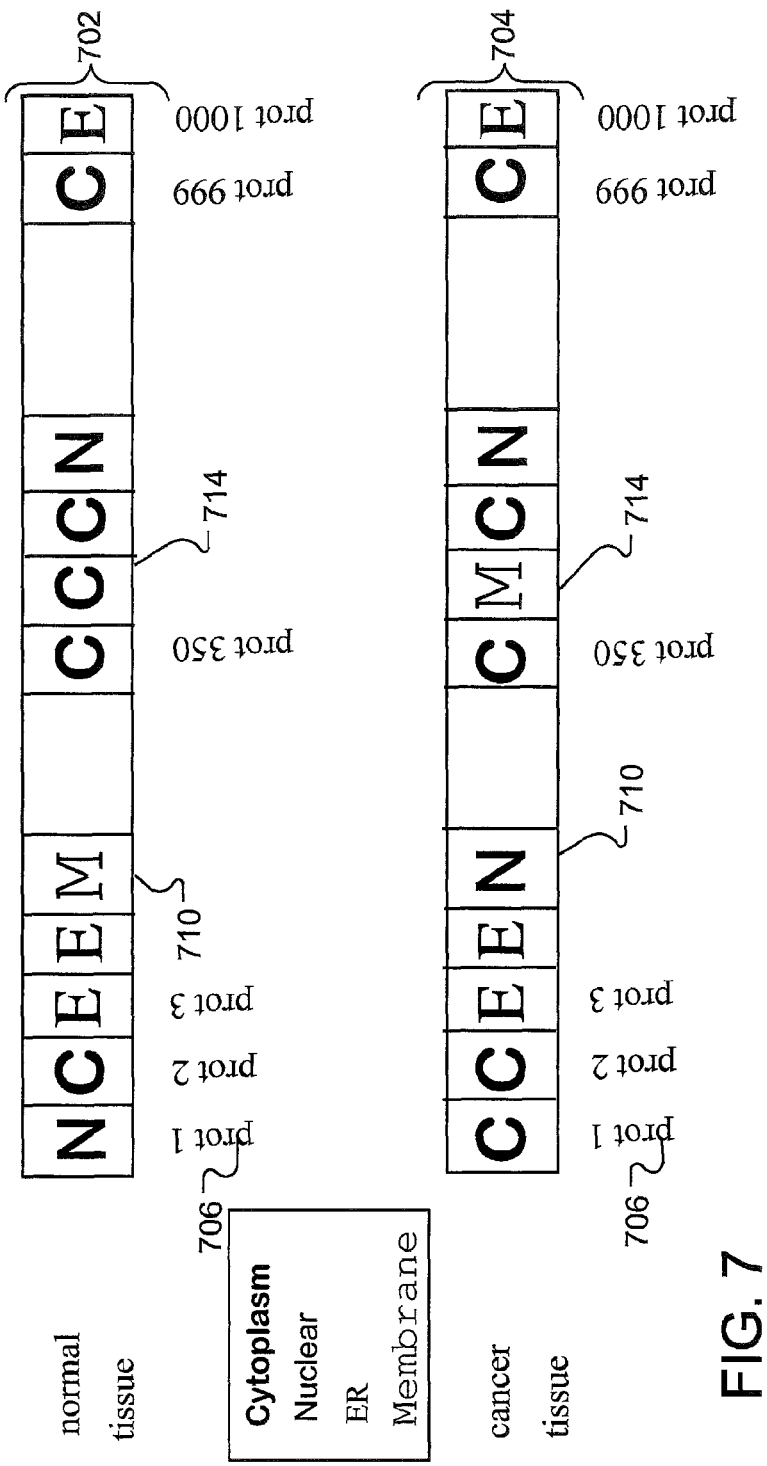
FIG. 7 is a diagram of an example of protein location diversity in tissues.

FIG. 7 is an example of protein location diversity in tissues 702, 704. In the example of FIG. 7, tissue 702 is healthy lung tissue. Tissue 704 is cancerous lung tissue. Tissues 702, 704 each include various proteins, including, e.g., protein$_1$-protein$_{1000}$. For a protein, location diversity engine 216 is configured to apply a classification technique to the features of the protein. Based on application of the classification technique, location diversity engine 216 is configured to classify the protein as belonging to one of the pre-defined locations of the cell.

In the example of FIG. 7, tissues 702, 704 each include proteins 706, 710, 714. Location diversity engine 216 determines a location for each of proteins 706, 710, 714 in tissue 702 and in tissue 704.

In this example, location diversity engine 216 classifies protein 706 as being located in a nucleus of a cell of tissue 702. Location diversity engine 216 classifies protein 706 as being located in cytoplasm of a cell of tissue 704. Location diversity engine 216 compares the location of protein 706 in tissue 702 to the location of protein 706 in tissue 704. Based on the comparison, location diversity engine 216 identifies protein 706 as a location biomarker, e.g., because the location of protein 706 in tissue 702 (e.g., the healthy lung tissue) differs from the location of protein 706 in tissue 704 (e.g., the cancerous lung tissue).

Location diversity engine 216 classifies protein 710 as being located in the membrane of the cell of tissue 702. Location diversity engine 216 classifies protein 710 as being located in the nucleus of the cell of tissue 704. Based on the difference in locations of protein 710 in tissues 702, 704, location diversity engine 216 identifies protein 710 as being a location biomarker.

Location diversity engine 216 classifies protein 714 as being located in the cytoplasm of a cell in tissue 702. Location diversity engine 216 classifies protein 714 as being located in the membrane of a cell in tissue 704. Based on the difference in locations of protein 714 in tissues 702, 704, location diversity engine 216 identifies protein 714 as being a location biomarker.

As previously described, location diversity engine 216 is configured to implement various classification techniques, including, e.g., a random forest (RF) classifier. The RF classifier includes an ensemble of classifiers (a "forest") that is generated by aggregating several different classification trees. In the RF classifier, a data point (represented as an input vector) is classified based on a majority vote gained by the input vector across the trees of the forest.

In an example, a tree of the forest is grown in various ways. For example, a bootstrapped sample (with replacement) of the training data is used to grow a tree. The sampling for bootstrapped data selection is done individually at each tree of the forest. In another example, for an M-dimensional input vector, a random subspace of m (<<M)-dimensions is selected, and the best split on this subspace is used to split a node of the trees.

In an example, location diversity engine 216 is configured to train a RF classifier. During training, location diversity engine 216 is configured to use two-thirds of the data points in training the RF classifier. The remaining one third of the data is used to obtain an unbiased estimate of the classification error as trees are added to the forest and to obtain estimates of variable importance.

In still another example, location diversity engine 216 is configured to implement a metaclassification technique to classify locations of proteins, e.g., in tissues 702, 704. The metaclassification technique uses pairwise classifiers. Generally, a pairwise classifier includes a classifier that is based on comparing entities in pairs to judge which entity is associated with a greater amount of a quantitative property. The metaclassification technique combines pairwise classifiers with RF classifiers to generate pairwise RF classifiers.

In this example, location diversity engine 216 uses the eleven subcellular locations to generate fifty-five pairwise RF classifiers. Using the pairwise RF classifiers, location diversity engine 216 generates a voted prediction of a subcellular location of a protein.

In an example, location diversity engine 216 is configured to train the pairwise RF classifiers to determine protein subcellular locations using one or more of images 204, 206, 302, 304, 402, 404. In training the pairwise RF classifiers, location diversity engine 216 generates a training set of images, e.g., from one or more of images 204, 206, 302, 304, 402, 404. Location diversity engine 216 also generates a testing set, e.g., to test the accuracy of a classifier being trained. In this example, a portion of images 204, 206, 302, 304, 402, 404 is selected for use in the training set and the remaining portion of images are included in the testing set.

In this example, the training set includes a set of training examples, including, e.g., a list of proteins with known classifications (e.g., subcellular location). Through application of a learning algorithm to the training set, the pairwise RF classifier learns the subcellular location of proteins in healthy tissue and the features of a protein that are indicative of a location of the protein in a cell. In this example, a learning algorithm analyzes the training set and produces an inferred function, e.g., the pairwise RF classifier. In this example, the inferred function predicts a correct output value for a valid input value.

In another example, location diversity engine 216 uses the testing set in determining the accuracy of the pairwise RF classifier being trained. In this example, location diversity engine 216 applies the trained pairwise RF classifier to the testing set and evaluates the accuracy of the resultant classifications.

As previously described, data repository 202 includes multiple different images of each tissue type. Location diversity engine 216 uses these images in training a classifier. In selecting images for inclusion in the training set or the testing set, location diversity engine 216 implements an antibody-based sampling (e.g., rather than the image-based sampling) to promote inclusion of the antibody image-instance in one of the training set or the testing set.

In an example, location diversity engine 216 is configured to classify a location of a protein into one of the eleven subcellular locations. In an example, location diversity engine 216 implements the metaclassification technique by obtaining a probability of membership in a subcellular location from a pairwise RF.classifier. In this example, the various probability values (e.g., the fifty-five distinct values from the pairwise comparisons) are inputs to the pairwise RF classifier.

In an example, location diversity engine 216 implements the metaclassification technique to output an 11-dimensional probability vector that denotes the probability of a protein occupying each of the eleven subcellular locations, including, e.g., a cytoplasm subcellular location, an endoplasmic reticulum (ER) subcellular location, a golgi subcellular location, an intermediate filament subcellular location, a lysosome subcellular location, a membrane subcellular location, a microtubules subcellular location, a mitochondria subcellular location, a nuclear subcellular location, a peroxisome subcellular location, and a secreted subcellular location.

In this example, location diversity engine 216 implements the metaclassification technique on the proteins identified in images 404, e.g., to determine a location of proteins in tissue 204. Location diversity engine 216 also implements the metaclassification technique on the proteins identified in other images (not shown) for tissue 206, e.g., to determine a location of proteins in tissue 206. Based on a comparison of the classified locations, location diversity engine 216 identifies location biomarkers for tissues depicted in images 204, 206 by identifying proteins with differing locations in the tissues depicted in images 204, 260.

Location diversity engine 216 is also configured to rank the proteins identified as location biomarkers, e.g., in accordance with entropy of membership to one of the subcellular locations. To promote a ranking of the location biomarkers, location diversity engine 216 generate an entropy value for the proteins identified as location biomarkers. Generally, an entropy value includes data indicative of an amount of unpredictability. In this example, proteins associated with a higher entropy value have increased uncertainty in classification to a subcellular location, e.g., relative to proteins associated with a lower entropy value. In this example, location diversity engine 216 generates a ranked list of location biomarkers in accordance with the entropy values associated with the proteins.

Clustering

As previously described, location diversity engine 216 is also configured to apply a clustering technique in identifying location biomarkers. Location diversity engine 216 is configured to implement various types of clustering techniques, including, e.g., a hierarchical clustering technique, a centroid-based clustering technique, a distribution-based clustering technique, a density-based clustering technique, and so forth.

In an example, location diversity engine 216 applies a hierarchical clustering technique. In this example, location diversity engine 216 generates a hierarchical tree based on features from images of healthy tissue (e.g., image 204). In this example, the hierarchical tree is generated using Euclidean distances between the various features of the healthy tissue. Location diversity engine 216 also selects a threshold value, e.g., based on the linkage distance between the features. In this example, the threshold value is selected such that 75% of proteins have three healthy images in a same cluster.

Location diversity engine 216 also uses the hierarchical tree to cluster cancer images (e.g., image 206). Location diversity engine 216 selects a protein as a location biomarker when the protein has a predefined number of healthy images in one cluster (e.g., three healthy images in one cluster) and another, different predefined number of cancer images in a different cluster (e.g., at least two cancer images in a different cluster).

In another example, location diversity engine 216 performs a clustering technique on the features of the proteins in a tissue. In this example, location diversity engine 216 generates clusters from features of a protein in healthy tissue, features of the protein in cancerous tissue and other features of other proteins in the tissue. Location diversity engine 216 determines that at least a portion of the features of the protein in the healthy tissue is assigned to a first cluster. Location diversity engine 216 also determines that at least a portion of the features of the protein in the cancerous tissue is assigned to a second cluster that differs from the first cluster.

In this example, location diversity engine 216 determines, based on at least the portion of the features of the protein in the cancerous tissue being assigned to the second cluster that differs from the first cluster, that the protein comprises a location biomarker.

In an example, location diversity engine 216 is also configured to perform one of more operations on identified location biomarkers. For example, location diversity engine 216 is configured to group together location biomarkers that are located in a same location of healthy tissue (e.g., the nucleus) and that are located in a same location of cancerous tissue (e.g., the membrane). Based on the groupings, location diversity engine 216 may determine patterns and/or statistics in the locations of location biomarkers in healthy tissue and in cancerous tissue. For example, location diversity engine 216 may determine that a particular percentage (e.g., 50%, 90% and so forth) of location biomarkers are located in the cytoplasm in healthy tissue but are located in the membrane in cancerous tissue.

Figure 8:
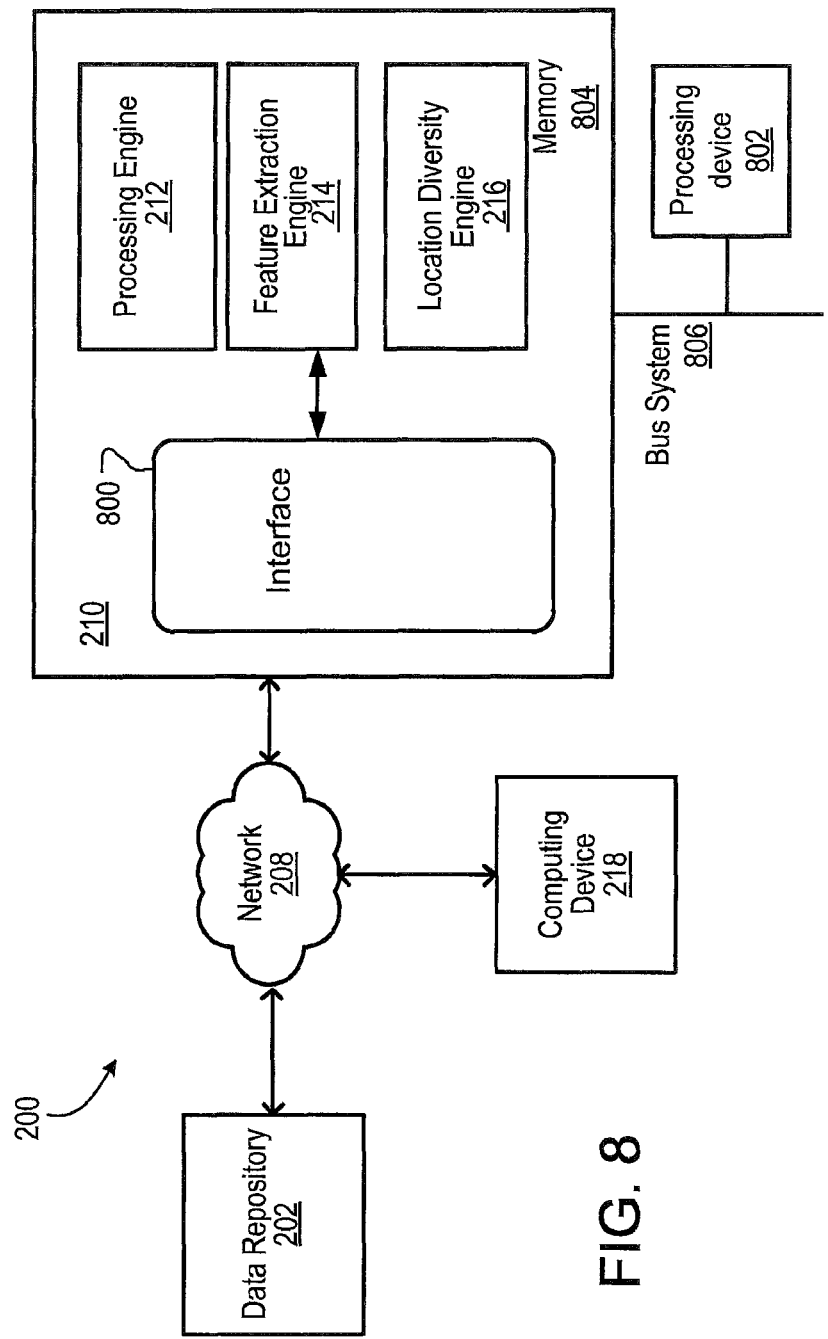
FIG. 8 is a block diagram showing examples of components of the network environment for detecting location biomarkers.

FIG. 8 is a block diagram showing examples of components of network environment 200 for detecting location biomarkers. In the example of FIG. 8, images 204, 206 and location biomarker message 220 are not shown.

Computing device 218 can be a computing device capable of taking input from a user and communicating over network 208 with server 210 and/or with other computing devices. For example, computing device 218 can be a mobile device, a desktop computer, a laptop, a cell phone, a personal digital assistant (PDA), a server, an embedded computing system, a mobile devices, and so forth.

Network 208 can include a large computer network, including, e.g., a local area network (LAN), wide area network (WAN), the Internet, a cellular network, or a combination thereof connecting a number of mobile computing devices, fixed computing devices, and server systems. The network(s) may provide for communications under various modes or protocols, including, e.g., Transmission Control Protocol/Internet Protocol (TCP/IP), Global System for Mobile communication (GSM) voice calls, Short Message Service (SMS), Enhanced Messaging Service (EMS), or Multimedia Messaging Service (MMS) messaging, Code Division Multiple Access (CDMA), Time Division Multiple Access (TDMA), Personal Digital Cellular (PDC), Wideband Code Division Multiple Access (WCDMA), CDMA2000, or General Packet Radio System (GPRS), among others. Communication may occur through a radio-frequency transceiver. In addition, short-range communication may occur, including, e.g., using a Bluetooth, WiFi, or other such transceiver.

Server 210 can be a variety of computing devices capable of receiving data and running one or more services, which can be accessed by computing device 218. In an example, server 210 can include a server, a distributed computing system, a desktop computer, a laptop, a cell phone, a rack-mounted server, and so forth. Server 210 can be a single server or a group of servers that are at a same location or at different locations.

Server 210 can receive data from computing device 218 and/or from data repository 202 through input/output (I/O) interface 800. I/O interface 800 can be a type of interface capable of receiving data over a network, including, e.g., an Ethernet interface, a wireless networking interface, a fiber-optic networking interface, a modem, and so forth. Server 210 also includes a processing device 802 and memory 804. A bus system 806, including, for example, a data bus and a motherboard, can be used to establish and to control data communication between the components of server 210.

Processing device 802 can include one or more microprocessors. Generally, processing device 802 can include an appropriate processor and/or logic that is capable of receiving and storing data, and of communicating over a network (not shown). Memory 804 can include a hard drive and a random access memory storage device, including, e.g., a dynamic random access memory, or other types of non-transitory machine-readable storage devices. As shown in FIG. 8, memory 804 stores computer programs that are executable by processing device 802. These computer programs include processing engine 212, feature extraction engine 214, and location diversity engine 216.

Figure 9:
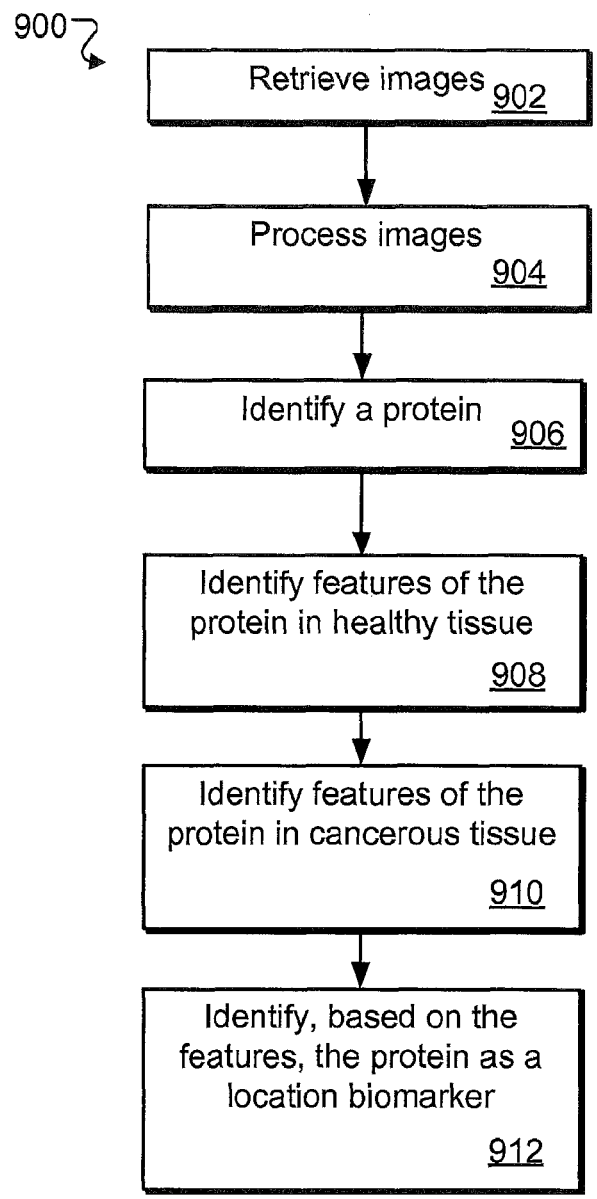
FIG. 9 is a flow chart of an example process for detecting location biomarkers.

FIG. 9 is a flow chart of an example process 900 for detecting location biomarkers. In operation, server 210 retrieves (902) from data repository 202 images 204, 206. Processing engine 212 processes (904) images 204, 206, e.g., by applying a spectral unmixing technique and a thresholding technique, as described above. Based on the processing of images 204, 206, processing engine 212 generates images 302, 304, 402, 402. Based on images 302, 304, 402, 402, processing engine 212 may identify DNA patterns and protein patterns in the tissues depicted in one or more images 204, 206.

In an example, processing engine 212 transmits (not shown) the DNA patterns, the protein patterns, and images 204, 206, 302, 304, 402, 404 (or any combination thereof) to feature extraction engine 214. Based on the DNA patterns, the protein patterns, and images 204, 206, 302, 304, 402, 404, feature extraction engine 214 identifies (906) a protein for which features are determined.

Using one or more of the DNA patterns, the protein patterns, and images 204, 206, 302, 304, 402, 404, feature extraction engine 214 identifies (908) features of the protein in the healthy tissue, e.g., the tissue depicted in image 204. Using one or more of the DNA patterns, the protein patterns, and images 204, 206, 302, 304, 402, 404, feature extraction engine 214 identifies (910) features of the protein in the cancerous tissue, e.g., the tissue depicted in image 206. As previously described, the identified features include (i) multiresolution texture features, (ii) nuclear overlap features, (iii) spacial proximity features, (iv) spatial co-occurrence (Haralick) features, (v) spatial statistics, and (vi) wavelet features.

In the example of FIG. 9, feature extraction engine 214 transmits (not shown) to location diversity engine 216 the identified features. Using the features of the protein in the cancerous tissue and the features of the protein in the healthy tissue, location diversity engine 216 identifies (912) the protein as a location biomarker, e.g., based on implementation of a classification technique, a clustering technique, a nonparametric hypothesis testing technique, and so forth. In this example, a location of the protein in the healthy tissue differs from a location of the protein in the cancerous tissue.

Using the techniques described herein, a system in configured to identify a protein as a location biomarker.

Figure 10:
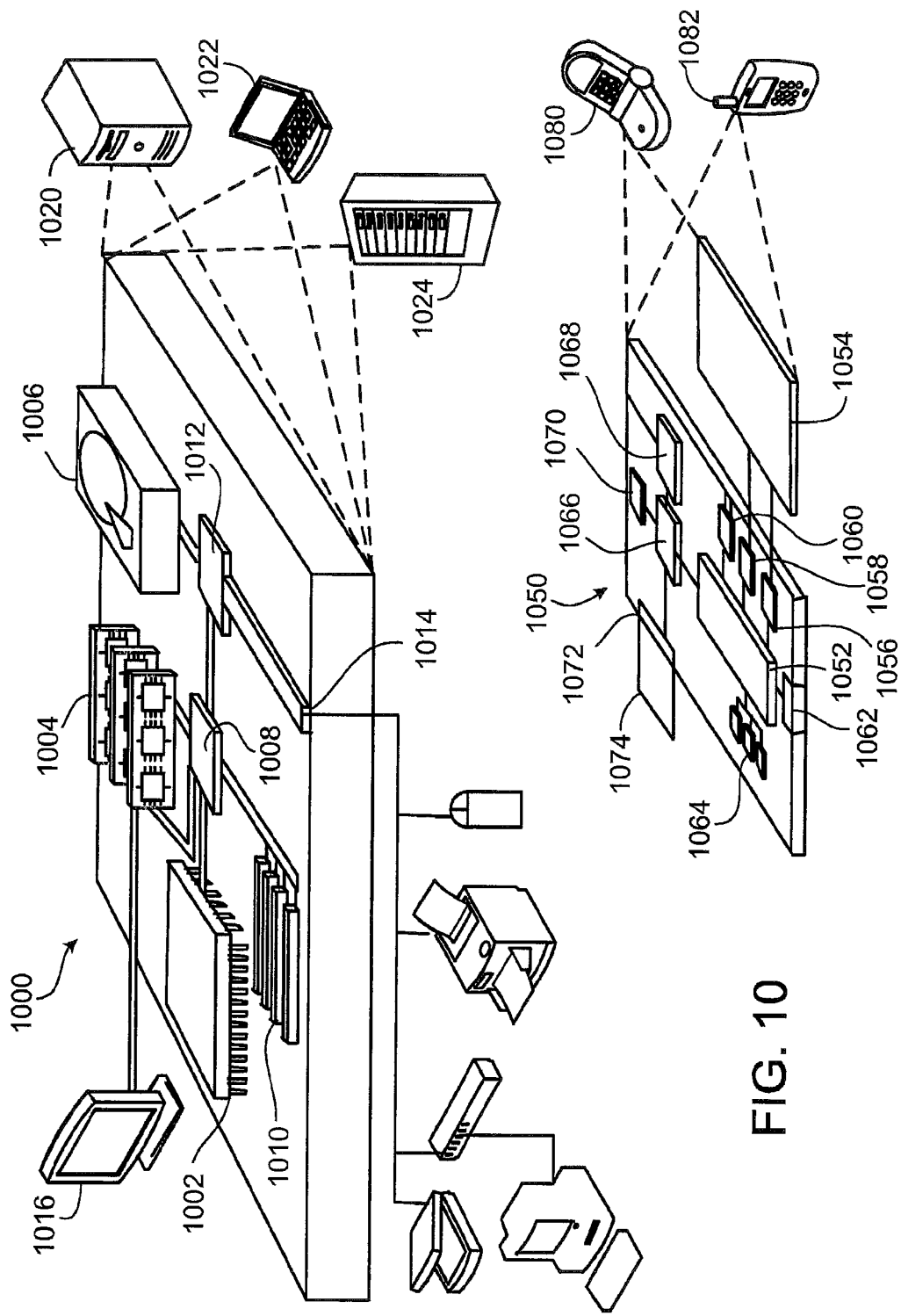
FIG. 10 shows an example of a computer device and a mobile computer device that can be used to implement the techniques described herein.

FIG. 10 shows an example of computer device 1000 and mobile computer device 1050, which can be used with the techniques described here. Computing device 1000 is intended to represent various forms of digital computers, such as laptops, desktops, workstations, personal digital assistants, servers, blade servers, mainframes, and other appropriate computers. Computing device 1050 is intended to represent various forms of mobile devices, such as personal digital assistants, cellular telephones, smartphones, and other similar computing devices. The components shown here, their connections and relationships, and their functions, are meant to be examples only, and are not meant to limit implementations of the techniques described and/or claimed in this document.

Computing device 1000 includes processor 1002, memory 1004, storage device 1006, high-speed interface 1008 connecting to memory 1004 and high-speed expansion ports 1010, and low speed interface 1012 connecting to low speed bus 1014 and storage device 1006. Each of components 1002, 1004, 1006, 1008, 1010, and 1012, are interconnected using various busses, and can be mounted on a common motherboard or in other manners as appropriate. Processor 1002 can process instructions for execution within computing device 1000, including instructions stored in memory 1004 or on storage device 1006 to display graphical data for a GUI on an external input/output device, such as display 1016 coupled to high speed interface 1008. In other implementations, multiple processors and/or multiple buses can be used, as appropriate, along with multiple memories and types of memory. Also, multiple computing devices 1000 can be connected, with each device providing portions of the necessary operations (e.g., as a server bank, a group of blade server; or a multi-processor system).

Memory 1004 stores data within computing device 1000. In one implementation, memory 1004 is a volatile memory unit or units. In another implementation, memory 1004 is a non-volatile memory unit or units. Memory 1004 also can be another form of computer-readable medium, such as a magnetic or optical disk.

Storage device 1006 is capable of providing mass storage for computing device 1000. In one implementation, storage device 1006 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in a data carrier. The computer program product also can contain instructions that, when executed, perform one or more methods, such as those described above. The data carrier is a computer- or machine-readable medium, such as memory 1004, storage device 1006, memory on processor 1002, and so forth.

High-speed controller 1008 manages bandwidth-intensive operations for computing device 1000, while low speed controller 1012 manages lower bandwidth-intensive operations. Such allocation of functions is an example only. In one implementation, high-speed controller 1008 is coupled to memory 1004, display 1016 (e.g., through a graphics processor or accelerator), and to high-speed expansion ports 1010, which can accept various expansion cards (not shown). In the implementation, low-speed controller 1012 is coupled to storage device 1006 and low-speed expansion port 1014. The low-speed expansion port, which can include various communication ports (e.g., USB, Bluetooth®, Ethernet, wireless Ethernet), can be coupled to one or more input/output devices, such as a keyboard, a pointing device, a scanner, or a networking device such as a switch or router, e.g., through a network adapter.

Computing device 1000 can be implemented in a number of different forms, as shown in the figure. For example, it can be implemented as standard server 1020, or multiple times in a group of such servers. It also can be implemented as part of rack server system 1024. In addition or as an alternative, it can be implemented in a personal computer such as laptop computer 1022. In some examples, components from computing device 1000 can be combined with other components in a mobile device (not shown), such as device 1050. Each of such devices can contain one or more of computing device 1000, 1050, and an entire system can be made up of multiple computing devices 1000, 1050 communicating with each other.

Computing device 1050 includes processor 1052, memory 1064, an input/output device such as display 1054, communication interface 1066, and transceiver 1068, among other components. Device 1050 also can be provided with a storage device, such as a microdrive or other device, to provide additional storage. Each of components 1050, 1052, 1064, 1054, 1066, and 1068, are interconnected using various buses, and several of the components can be mounted on a common motherboard or in other manners as appropriate.

Processor 1052 can execute instructions within computing device 1050, including instructions stored in memory 1064. The processor can be implemented as a chipset of chips that include separate and multiple analog and digital processors. The processor can provide, for example, for coordination of the other components of device 1050, such as control of user interfaces, applications run by device 1050, and wireless communication by device 1050.

Processor 1052 can communicate with a user through control interface 1058 and display interface 1056 coupled to display 1054. Display 1054 can be, for example, a TFT LCD (Thin-Film-Transistor Liquid Crystal Display) or an OLED (Organic Light Emitting Diode) display, or other appropriate display technology. Display interface 1056 can comprise appropriate circuitry for driving display 1054 to present graphical and other data to a user. Control interface 1058 can receive commands from a user and convert them for submission to processor 1052. In addition, external interface 1062 can communicate with processor 1042, so as to enable near area communication of device 1050 with other devices. External interface 1062 can provide, for example, for wired communication in some implementations, or for wireless communication in other implementations, and multiple interfaces also can be used.

Memory 1064 stores data within computing device 1050. Memory 1064 can be implemented as one or more of a computer-readable medium or media, a volatile memory unit or units, or a non-volatile memory unit or units. Expansion memory 1074 also can be provided and connected to device 1050 through expansion interface 1072, which can include, for example, a SIMM (Single In Line Memory Module) card interface. Such expansion memory 1074 can provide extra storage space for device 1050, or also can store applications or other data for device 1050. Specifically, expansion memory 1074 can include instructions to carry out or supplement the processes described above, and can include secure data also. Thus, for example, expansion memory 1074 can be provide as a security module for device 1050, and can be programmed with instructions that permit secure use of device 1050. In addition, secure applications can be provided via the SIMM cards, along with additional data, such as placing identifying data on the SIMM card in a non-hackable manner.

The memory can include, for example, flash memory and/or NVRAM memory, as discussed below. In one implementation, a computer program product is tangibly embodied in a data carrier. The computer program product contains instructions that, when executed, perform one or more methods, such as those described above. The data carrier is a computer- or machine-readable medium, such as memory 1064, expansion memory 1074, and/or memory on processor 1052, that can be received, for example, over transceiver 1068 or external interface 1062.

Device 1050 can communicate wirelessly through communication interface 1066, which can include digital signal processing circuitry where necessary. Communication interface 1066 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 1068. In addition, short-range communication can occur, such as using a Bluetooth®, WiFi, or other such transceiver (not shown). In addition, GPS (Global Positioning System) receiver module 1070 can provide additional navigation- and location-related wireless data to device 1050, which can be used as appropriate by applications running on device 1050.

Device 1050 also can communicate audibly using audio codec 1060, which can receive spoken data from a user and convert it to usable digital data. Audio codec 1060 can likewise generate audible sound for a user, such as through a speaker, e.g., in a handset of device 1050. Such sound can include sound from voice telephone calls, can include recorded sound (e.g., voice messages, music files, and so forth) and also can include sound generated by applications operating on device 1050.

Computing device 1050 can be implemented in a number of different forms, as shown in the figure. For example, it can be implemented as cellular telephone 1080. It also can be implemented as part of smartphone 1082, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described here can be implemented on a computer having a display device (e.g., a CRT (cathode ray tube) or LCD (liquid crystal display) monitor) for displaying data to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the engines described herein can be separated, combined or incorporated into a single or combined engine. The engines depicted in the figures are not intended to limit the systems described here to the software architectures shown in the figures.

A number of embodiments have been described. Nevertheless, it will be understood that various modifications can be made without departing from the spirit and scope of the processes and techniques described herein.

In some embodiments the present invention provides methods for diagnosing cancer in a subject, the methods comprising comparing the placement of a location biomarker in a control sample to the placement of the location biomarker in a sample from the subject. In some embodiments, subject samples in which the placement of the location biomarker is the same as the placement of the location biomarker in a control sample comprising cancerous cells is indicative of the presence of cancer in the patient. In some embodiments, subject samples in which the placement of the location biomarker is different from the placement of the location biomarker in a control sample comprising non-cancerous cells is indicative of the presence of cancer in the patient.

The present invention further provides methods for treating a patient comprising determining whether a patient has cancer according to the methods described supra and infra and treating the patient with a therapeutically effective amount of a traditional cancer medications if the patient is diagnosed as having cancer. The methods of the present invention also find utility, for example, in theranostics and in the fields of drug discovery for identifying new potential targets for therapeutics.

In another example, FIG. 11 lists location biomarkers along with gene names and exemplary accession numbers, the entire contents of which are incorporated herein by reference.

In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

What is claimed is:

1. A method performed by one or more processing devices, comprising:
retrieving data for a protein in a tissue type in a first state and for the protein in the tissue type in a second state;
determining, based on the retrieved data, first features of the protein in the tissue type in the first state;
determining, based on the retrieved, second features of the protein in the tissue type in the second state; and
identifying, based on the first features and the second features, that a location of the protein in the tissue type in the first state differs from a location of the protein in the tissue type in the second state.

2. The method of claim 1, wherein the tissue type in the first state comprises a type of tissue with cancerous cells, and wherein the tissue type in the second state comprises the type of tissue without a measurable amount of cancerous cells.

3. The method of claim 1, wherein retrieving the data comprises:
retrieving, from a data repository, a first image of the protein in the tissue type in the first state and a second image of the protein in the tissue type in the second state.

4. The method of claim 3, wherein processing the data comprises one or more of:
performing spectral unmixing on the first and second images; and
applying a thresholding technique to the first and second images.

5. The method of claim 1, wherein the protein identified as having the location in the tissue type in the first state that differs from the location of the protein in the tissue type in the second state comprises a location biomarker.

6. The method of claim 1, wherein retrieving the data comprises retrieving a first set of images and a second set of images, wherein the first features are associated with the first set of images, wherein the second features are associated with the second set of images, and wherein identifying comprises:
performing nonparametric hypothesis testing on the first set and on the second set;
determining a difference between the first set and the second set; and
determining, based on the difference, that the protein comprises a location biomarker.

7. The method of claim 1, wherein retrieving the data comprises retrieving a first set of images of the protein and a second set of images of the protein, wherein the first features are associated with the first set of images, wherein the second features are associated with the second set of images, and wherein identifying comprises:
generating clusters from the first set, the second set and images of other proteins in the tissue type in the first state and the tissue type in the second state;
determining that at least a first image from the first set is assigned to a first cluster;
determining that at least a second image from the second set is assigned to a second cluster that differs from the first cluster; and
determining, based on the second cluster differing from the first cluster, that the protein comprises a location biomarker.

8. The method of claim 1, wherein identifying comprises:
generating, based on the first features, a first classification indicative of the location of the protein in the tissue type in the first state;
generating, based on the second features, a second classification indicative of the location of the protein in the tissue type in the second state;
comparing the first classification to the second classification;
determining, based on the comparing, that the first classification differs from the second classification; and
determining, based on the first classification differing from the second classification, that the protein comprises a location biomarker.

9. The method of claim 8, wherein generating the first classification and the second classification are based on a classifier, and wherein the method further comprises:
training the classifier by performing operations comprising:
generating a training set of data from images of healthy tissue retrieved from a data repository, wherein the training set comprises data indicative of locations of proteins in the noncancerous tissue;
applying a learning algorithm to the training set; and
evaluating results of application of the learning algorithm to the training set.

10. The method of claim 8, wherein one or more of the first classification and the second classification comprises a classification to a subcellular location, wherein the subcellular location comprises one of a cytoplasm subcellular location, an endoplasmic reticulum (ER) subcellular location, a golgi subcellular location, an intermediate filament subcellular location, a lysosome subcellular location, a membrane subcellular location, a microtubules subcellular location, a mitochondria subcellular location, a nuclear subcellular location, a peroxisome subcellular location, and a secreted subcellular location.

11. The method of claim 1, wherein the tissue type comprises one of: salivary gland tissue; thyroid gland tissue; parathyroid gland tissue; breast tissue; liver tissue; gall bladder tissue; pancreas tissue; adrenal gland tissue; kidney tissue; urinary tract tissue; ovary tissue; fallopian tube tissue; endometrium tissue; placenta tissue; uterine tissue; vaginal tissue; vulva tissue; lateral ventricle wall tissue; cerebral cortex tissue; hippocampus tissue; cerebellum tissue; skin tissue; bone marrow tissue; skeletal muscle tissue; smooth muscle tissue; lymph node tissue; oral mucosa tissue; tonsil tissue; esophagus tissue; bronchus tissue; lung tissue; heart muscle tissue; spleen tissue; stomach tissue; duodenum tissue; small intestine tissue; appendix tissue; colon tissue; rectum tissue; seminal vesicle tissue; prostate tissue; testis tissue; and epidydimis tissue.

12. The method of claim 1, wherein the tissue type in the first state comprises a type of tissue with cancer, wherein the cancer comprises one or more of prostate cancer, lung cancer, colon cancer, rectum cancer, urinary bladder cancer, melanoma, non-Hodgkin lymphoma, kidney cancer, renal pelvis cancer, oral cavity cancer, pharynx cancer, leukemia, pancreas cancer, uterine cancer, thyroid cancer, and ovarian cancer.

13. The method of claim 1, wherein determining the first protein pattern and the second protein pattern comprises:
determining, based on processing the data, a first protein pattern for the protein in the tissue type in the first state and a second protein pattern for the protein in the tissue type in the second state.

14. The method of claim 1, wherein the protein comprises a location biomarker, and wherein the method further comprises:
  grouping together location biomarkers that are located in a same location of the tissue type of the first state and that are located in a same location of the tissue type of the second state.

15. The method of claim 1, wherein one or more of the first features and the second features comprise one or more of (i) multiresolution texture features, (ii) nuclear overlap features, (iii) spacial proximity features, (iv) spatial co-occurrence (Haralick) features, (v) spatial statistics, and (vi) wavelet features.

16. The method of claim 1, wherein the retrieved data comprises one or more images, and wherein the method further comprises:
  selecting a portion of an image for processing.

17. The method of claim 16, wherein the selected portion comprises one or more of:
  an increased concentration of visual signals relative to a concentration of other visual signals in other portions of the image; and
  an increased quality of visual signals relative to a quality of other visual signals in other portions of the image.

18. One or more Non-transitory machine-readable media configured to store instructions that are executable by one or more processing devices to perform operations comprising: retrieving data for a protein in a tissue type in a first state and for the protein in the tissue type in a second state; determining, based on the retrieved data, first features of the protein in the tissue type in the first state; determining, based on the retrieved, second features of the protein in the tissue type in the second state; and identifying, based on the first features and the second features, that a location of the protein in the tissue type in the first state differs from a location of the protein in the tissue type in the second state.

19. The one or more machine-readable media of claim 18, wherein the tissue type in the first state comprises a type of tissue with cancerous cells, and wherein the tissue type in the second state comprises the type of tissue without a measurable amount of cancerous cells.

20. The one or more machine-readable media of claim 18, wherein retrieving the data comprises:
  retrieving, from a data repository, a first image of the protein in the tissue type in the first state and a second image of the protein in the tissue type in the second state.

21. The one or more machine-readable media of claim 18, wherein the protein identified as having the location in the tissue type in the first state that differs from the location of the protein in the tissue type in the second state comprises a location biomarker.

22. The one or more machine-readable media of claim 18, wherein retrieving the data comprises retrieving a first set of images and a second set of images, wherein the first features are associated with the first set of images, wherein the second features are associated with the second set of images, and wherein identifying comprises:
  performing nonparametric hypothesis testing on the first set and on the second set;
  determining a difference between the first set and the second set; and
  determining, based on the difference, that the protein comprises a location biomarker.

23. The one or more machine-readable media of claim 18, wherein retrieving the data comprises retrieving a first set of images of the protein and a second set of images of the protein, wherein the first features are associated with the first set of images, wherein the second features are associated with the second set of images, and wherein identifying comprises:
  generating clusters from the first set, the second set and images of other proteins in the tissue type in the first state and the tissue type in the second state;
  determining that at least a first image from the first set is assigned to a first cluster;
  determining that at least a second image from the second set is assigned to a second cluster that differs from the first cluster; and
  determining, based on the second cluster differing from the first cluster, that the protein comprises a location biomarker.

24. The one or more machine-readable media of claim 18, wherein identifying comprises:
  generating, based on the first features, a first classification indicative of the location of the protein in the tissue type in the first state;
  generating, based on the second features, a second classification indicative of the location of the protein in the tissue type in the second state;
  comparing the first classification to the second classification;
  determining, based on the comparing, that the first classification differs from the second classification; and
  determining, based on the first classification differing from the second classification, that the protein comprises a location biomarker.

25. An electronic system comprising:
  one or more processing devices; and
  one or more machine-readable media configured to store instructions that are executable by the one or more processing devices to perform operations comprising:
    retrieving data for a protein in a tissue type in a first state and for the protein in the tissue type in a second state;
    determining, based on the retrieved data, first features of the protein in the tissue type in the first state;
    determining, based on the retrieved, second features of the protein in the tissue type in the second state; and
    identifying, based on the first features and the second features, that a location of the protein in the tissue type in the first state differs from a location of the protein in the tissue type in the second state.

26. The electronic system of claim 25, wherein the tissue type in the first state comprises a type of tissue with cancerous cells, and wherein the tissue type in the second state comprises the type of tissue without a measurable amount of cancerous cells.

27. The electronic system of claim 25, wherein retrieving the data comprises:
  retrieving, from a data repository, a first image of the protein in the tissue type in the first state and a second image of the protein in the tissue type in the second state.

28. The electronic system of claim 25, wherein the protein identified as having the location in the tissue type in the first state that differs from the location of the protein in the tissue type in the second state comprises a location biomarker.

29. The electronic system of claim 25, wherein retrieving the data comprises retrieving a first set of images and a second set of images, wherein the first features are associated with the first set of images, wherein the second features are associated with the second set of images, and wherein identifying comprises:
  performing nonparametric hypothesis testing on the first set and on the second set;
  determining a difference between the first set and the second set; and determining, based on the difference, that the protein comprises a location biomarker.

30. The electronic system of claim 25, wherein retrieving the data comprises retrieving a first set of images of the protein and a second set of images of the protein, wherein the first features are associated with the first set of images, wherein the second features are associated with the second set of images, and wherein identifying comprises:
- generating clusters from the first set, the second set and images of other proteins in the tissue type in the first state and the tissue type in the second state;
- determining that at least a first image from the first set is assigned to a first cluster;
- determining that at least a second image from the second set is assigned to a second cluster that differs from the first cluster; and
- determining, based on the second cluster differing from the first cluster, that the protein comprises a location biomarker.

31. The electronic system of claim 25, wherein identifying comprises:
- generating, based on the first features, a first classification indicative of the location of the protein in the tissue type in the first state;
- generating, based on the second features, a second classification indicative of the location of the protein in the tissue type in the second state;
- comparing the first classification to the second classification;
- determining, based on the comparing, that the first classification differs from the second classification; and
- determining, based on the first classification differing from the second classification, that the protein comprises a location biomarker.

* * * * *

UNITED STATES PATENT AND TRADEMARK OFFICE
CERTIFICATE OF CORRECTION

PATENT NO. : 9,092,850 B2  
APPLICATION NO. : 13/980512  
DATED : July 28, 2015  
INVENTOR(S) : Robert F. Murphy et al.

Page 1 of 1

It is certified that error appears in the above-identified patent and that said Letters Patent is hereby corrected as shown below:

In the Claims

Col. 24, line 53-54, claim 11, delete "epidydimis" and insert -- epididymis --

Col. 25, line 11, claim 15, delete "spacial" and insert -- spatial --

Col. 25, line 25, claim 18, delete "Non-transitory" and insert -- non-transitory --

Signed and Sealed this  
Twenty-first Day of June, 2016

Michelle K. Lee  
*Director of the United States Patent and Trademark Office*